United States Patent [19]

Michiels et al.

[11] Patent Number: 5,639,948
[45] Date of Patent: Jun. 17, 1997

[54] STAMEN-SPECIFIC PROMOTERS FROM RICE

[75] Inventors: Frank Michiels, Bottelare, Belgium; Sinji Morioka, Iwata, Japan; Trees Scheirlinck, Oosterzele, Belgium; Toshihiko Komari, Iwata, Japan

[73] Assignee: Plant Genetic Systems, N.V., Brussels, Belgium

[21] Appl. No.: 104,072

[22] PCT Filed: Feb. 6, 1992

[86] PCT No.: PCT/EP92/00274

§ 371 Date: Oct. 4, 1993

§ 102(e) Date: Oct. 4, 1993

[87] PCT Pub. No.: WO92/13956

PCT Pub. Date: Aug. 20, 1992

[30] Foreign Application Priority Data

Feb. 8, 1991 [EP] European Pat. Off. ............. 91400318
Sep. 27, 1991 [EP] European Pat. Off. ............. 91402590
Dec. 10, 1991 [EP] European Pat. Off. ............. 91403352

[51] Int. Cl.⁶ .......................... C12N 15/00; C12N 15/82; A01H 1/06; A01M 4/00

[52] U.S. Cl. .................. 800/205; 435/172.3; 435/172.1; 435/419; 435/414; 935/36; 935/35; 935/67; 47/58; 47/DIG. 1; 536/24.1; 536/23.2; 536/23.6

[58] Field of Search .................. 800/205; 435/172.3, 435/172.1, 240.4; 935/36, 35, 67; 47/58, DIG. 2

[56] References Cited

FOREIGN PATENT DOCUMENTS 344029 11/1989 European Pat. Off. .

OTHER PUBLICATIONS

Tchang et al. "Phospholipid Transfer Protein: Full–Length cDNA and Amino Acid Sequence in Maize". vol. 263, No. 32 pp. 16849–16855 Nov. 15, 1988.

*Primary Examiner*—Gary Benzion
*Attorney, Agent, or Firm*—Merchant, Gould, Smith, Edell, Welter & Schmidt, P.A.

[57] ABSTRACT

Rice anther-specific promoters which are of particular utility in the production of transgenic male-sterile monocots and plants for restoring their fertility.

23 Claims, No Drawings

1

STAMEN-SPECIFIC PROMOTERS FROM RICE

This invention relates to promoters isolated from rice which can provide gene expression predominantly or specifically in stamen cells of a plant, particularly a monocotyledonous plant, and thereby provide little or no gene expression in other parts of the plant that are not involved in the production of fertile pollen. The promoters are useful in the production of transformed plants, in which a gene is to be expressed at least predominantly, and preferably specifically, in the stamen cells, preferably in the anther cells. The promoters are especially useful in the production of male-sterile plants and male fertility-restorer plants as described in European patent applications ("EPA") 89401194.9 and 90402281.1, respectively (which are incorporated herein by reference), particularly in the production of hybrids of monocotyledonous plants, such as corn, rice or wheat.

SUMMARY OF THE INVENTION

In accordance with this invention are provided male flower-specific cDNA sequences isolated from rice comprising the sequences: SEQ ID no. 1, SEQ ID no. 2, SEQ ID no. 3, SEQ ID no. 4 and SEQ ID no. 5 shown in the Sequence Listing. Also in accordance with this invention are provided the stamen-specific, preferably anther-specific, particularly tapetum-specific, promoters of the rice genes corresponding to such cDNA sequences, particularly the promoter PT72 upstream from nucleotide 2846 of SEQ ID no. 6, the promoter PT42 upstream from nucleotide 1809 of SEQ ID no. 7, and the promoter PE1 upstream from nucleotide 2264 of SEQ ID no. 8 shown in the Sequence Listing. These promoters can each be used in a foreign DNA sequence, preferably a foreign chimaeric DNA sequence, which contains a structural gene, preferably a male-sterility DNA or a male fertility-restorer DNA, under the transcriptional control of one of the promoters and which can be used to transform the nuclear genome of a cell of a plant, particularly a monocotyledonous plant. Further in accordance with this invention are provided: the male-sterile plant or male fertility-restorer plant which can be regenerated from such a cell transformed with the foreign DNA sequence of this invention; the cells, cell cultures and seeds of such a plant; and the male fertility-restored plant and its seeds resulting from crossing such male-sterile and male fertility-restorer plants.

DETAILED DESCRIPTION OF THE INVENTION

In accordance with this invention, a male-sterile plant or a male fertility-restorer plant can be produced from a single cell of a plant by transforming the plant cell in a known manner to stably insert, into its nuclear genome, the foreign DNA sequence of this invention. The foreign DNA sequence comprises at least one male-sterility DNA or male fertility-restorer DNA that is: under the control of, and fused in frame at its upstream (i.e., 5') end to, one of the stamen-specific, preferably anther-specific, particularly tapetum-specific, promoters of this invention; and fused at its downstream (i.e., 3') end to suitable transcription termination (or regulation) signals, including a polyadenylation signal. Thereby, the RNA and/or protein or polypeptide, encoded by the male-sterility or fertility-restorer DNA is produced or overproduced at least predominantly, preferably exclusively, in stamen cells of the plant. The foreign DNA sequence can also comprise at least one marker DNA that: encodes a RNA and/or protein or polypeptide which, when present at least in a specific tissue or specific cells of the plant, renders the plant easily separable or distinguishable from other plants which do not contain such RNA and/or protein or polypeptide at least in the specific tissue or specific cells; is under the control of, and is fused at its 5' end to, a second promoter which is capable of directing expression of the marker DNA at least in the specific tissue or specific cells; and is fused at its 3' end to suitable transcription termination signals, including a polyadenylation signal. The marker DNA is preferably in the same genetic locus as the male-sterility or fertility-restorer DNA. This linkage between the male-sterility or fertility-restorer DNA and the marker DNA guarantees, with a high degree of certainty, the joint segregation of both the male-sterility or fertility-restorer DNA and the marker DNA into offspring of the plant regenerated from the transformed plant cell. However, in some cases, such joint segregation is not desirable, and the marker DNA should be in a different genetic locus from the male-sterility or fertility-restorer DNA.

The male-sterility DNA of this invention can be any gene or gene fragment, whose expression product (RNA and/or protein or polypeptide) disturbs significantly the metabolism, functioning and/or development of stamen cells, preferably anther cells, and thus prevents the production of fertile pollen. Preferred male-sterility DNAs are described in EPA 89401194.9, for example those DNAs encoding: RNases such as RNase T1 or barnase; DNases such as endonucleases (e.g., EcoRI); proteases such as papain; enzymes which catalyse the synthesis of phytohormones (e.g. isopentenyl transferase or the gene products of gene 1 and gene 2 of the T-DNA of Agrobacterium; glucanases; lipases; lipid peroxidases; plant cell wall inhibitors; or toxins (e.g., the A-fragment of diphteria toxin or botulin). Other preferred examples of male-sterility DNAs are antisense DNAs encoding RNAs complementary to genes, the products of which are essential for the normal development of fertile pollen. Further preferred examples of male sterility DNAs encode ribozymes capable of cleaving specifically given target sequences of genes encoding products which are essential for the production of fertile pollen. Still other examples of male-sterility DNAs encode products which can render stamen cells, particularly anther cells—and not other parts of the plant—susceptible to specific diseases (e.g. fungi or virus infection) or stress conditions (e.g. herbicides).

The construction of a vector comprising a male-sterility DNA, such as a barnase-encoding DNA, under the control of a rice anther-specific promoter of this invention is most conveniently effected in a bacterial host organism such as $E.$ $coli$. However, depending on the nature of the male-sterility DNA and the specific configuration of the vector, problems can be encountered due to the expression of the male-sterility DNA in, and the concurrent decrease of viability of, the host organism. Such problems can be solved in a number of ways. For instance, the host organism can be provided, on the same or different plasmid from that containing the male-sterility DNA or even on its chromosomal DNA, with another DNA sequence that prevents or inhibits significantly the effect of the expression of the male-sterility DNA in the host organism. Such an other DNA sequence can encode, for example: an antisense RNA so that the accumulation and translation of the male-sterility RNA is prevented; or a protein (e.g., barstar) which specifically inhibits the gene product of the male-sterility DNA (e.g., barnase; Hartley (1988) J. Mol. Biol. 202, 913). Alternatively, the male-sterility DNA can contain an element, such as a plant intron, which will only result in an active gene product in a plant cell environment. Examples of introns that can be used for this purpose are introns of: the transcriptional units of the adh-1 gene of maize (Luehrsen and Walbot (1991) Mol. Gen. Genet. 225, 81; Mascarenhas et al (1990) Plant Mol. Biol. 15, 913), the shrunken-1 gene of maize (Vasil et al (1989) Plant Physiol. 91, 1575), the cat-1 gene of castor bean (Tanaka et al (1990) Nucleic Acids Research ("NAR") 18, 6767), and the act-1 gene of rice (McElroy et al (1990) The Plant Cell 2, 163; PCT publication WO 91/09948).

The male fertility-restorer DNA of this invention can be any gene or gene fragment, whose expression product (RNA and/or protein or polypeptide) inactivates, neutralizes, inhibits, blocks, offsets, overcomes or otherwise prevents the specific activity of the product of a male-sterility DNA in stamen cells, particularly in anther cells. Preferred fertility-restorer DNAs are described in EPA 90402281.1, for example those DNAs encoding: barstar which is the inhibitor of barnase; EcoRI methylase which prevents the activity of EcoRI; or protease inhibitors (e.g., the inhibitors of papain). Other examples of fertility-restorer DNAs are antisense DNAs encoding RNAs complementary to male-sterility DNAs. Further examples of fertility-restorer DNAs encode ribozymes capable of cleaving specifically given target sequences encoded by male-sterility DNAs.

The marker DNA of this invention can be any gene or gene fragment encoding an RNA and/or protein or polypeptide that allows plants, expressing the marker DNA, to be easily distinguished and separated from plants not expressing the marker DNA. Examples of the marker DNA are described in EPA 89401194.9, such as marker DNAs which encode proteins or polypeptides that: provide a distinguishable color to plant cells, such as the A1 gene encoding dihydroquercetin-4-reductase (Meyer et al (1987) Nature 330, 677-678) and the glucuronidase gene (Jefferson et al (1988) Proc. Natl. Acad. Sci. USA ("PNAS") 83, 8447); provide a specific morphological characteristic to a plant such as dwarf growth or a different shape of the leaves; confer on a plant stress tolerance, such as is provided by the gene encoding superoxide dismutase as described in EPA 88402222.9; confer disease or pest resistance on a plant, such as is provided by a gene encoding a *Bacillus thuringiensis* endotoxin conferring insect resistance on a plant, as described in EPA 86300291.1; or confer on a plant a bacterial resistance, such as is provided by the bacterial peptide described in EPA 88401673.4. Preferred marker DNAs encode proteins of polypeptides inhibiting or neutralizing the activity of herbicides such as: the sfr gene and the sfrv gene encoding enzymes conferring resistance to glutamine synthetase inhibitors such as Bialaphos and phosphinotricine as described in EPA 87400544.0.

In order for the protein or polypeptide encoded by the marker DNA to function as intended, it is often preferred to have it produced in the plant cell as a precursor, in which the mature protein is linked at its N-terminal end to another polypeptide (a "targeting peptide") which will translocate the mature protein to a specific compartment such as the chloroplasts, the mitochondria, or the endoplasmic reticulum. Such targeting peptides and DNA sequences coding for them (the "targeting sequences") are well known. For example, if a marker DNA codes for a protein that confers tolerance or resistance to a herbicide or another selective agent that acts on chloroplast metabolism, such as the sfr (or bar) gene or the sfrv gene (European patent publication ["EP"] 0,242,236), it may be preferred that such gene also comprise a chloroplast targeting sequence such as that coding for the transit peptide of the small subunit of the enzyme 1,5-ribulose bisphosphate carboxylase (Krebbers et al (1988) Plant Mol. Biol. 11, 745; EPA 85402596.2), although other targeting sequences coding for other transit peptides, such as those listed by Von Heijne et al (1991) Plant Mol. Biol. Reporter 9, 104, can be used.

The stamen-specific, preferably anther-specific, promoters of this invention, such as the promoter PT72 upstream from nucleotide 2846 of SEQ ID no. 6, the promoter PT42 upstream from nucleotide 1809 of SEQ ID no. 7, and the promoter PE1 upstream from nucleotide 2264 of SEQ ID no. 8—which can be used to control the male-sterility DNA or the fertility-restorer DNA—can be identified and isolated in a well known manner as described in EPA 89401194.9. In this regard, each of the cDNAs of SEQ ID nos. 1 to 5 of this invention can be used as a probe to identify (i.e., to hybridize to) the corresponding region of the rice genome (i.e., the region containing DNA coding for the stamen-specific mRNA, from which the cDNA was made). Then, the portion of the plant genome that is upstream (i.e., 5') from the DNA coding for such stamen-specific mRNA and that contains the promoter of this DNA can be identified.

The second promoter, which controls the marker DNA, can also be selected and isolated in a well known manner, for example as described in EPA 89401194.9, so that the marker DNA is expressed either selectively in one or more specific tissues or cells or constitutively in the entire plant, as desired, depending on the nature of the RNA and/or protein or polypeptide encoded by the marker DNA.

In the foreign DNA sequence of this invention, 3' transcription termination signals or the "3' end" can be selected from among those which are capable of providing correct transcription termination and/or polyadenylation of mRNA in plant cells. The transcription termination signals can be the natural ones of the male-sterility or fertility-restorer DNA, to be transcribed, or can be foreign or heterologous. Examples of heterologous 3' transcription termination signals are those of the octopine synthase gene (Gielen et al (1984) EMBO J. 3, 835–845) and of the T-DNA gene 7 (Velten and Schell (1985) NAR 13, 6981–6998). When the foreign DNA sequence of this invention comprises more than one structural gene (e.g., a male-sterility or fertility-restorer DNA and a marker DNA), it is preferred that the 3' ends of the structural genes be different.

In plants, especially in monocotyledonous plants, particularly cereals such as rice, corn and wheat, the expression in accordance with this invention of a marker DNA, as well as a male-sterility DNA or a fertility-restorer DNA, can be enhanced by the presence at one or more, preferably one, appropriate position(s) in the transcriptional unit of each foreign DNA sequence of this invention of a suitable plant intron (Luehrsen and Walbot (1991) Mol. Gen. Genet. 225, 81; Mascarenhas et al (1990) Plant Mol. Biol. 15, 913; Vasil et al (1989) Plant Physiol. 91, 1575; Tanaka et al (1990) NAR 18, 6767; McElroy et al (1990) The Plant Cell 2, 163; PCT publication WO 91/09948). Preferably, each intron has a nucleotide sequence that: is recognizable by the cells of the plant species being transformed (for requirements of intron recognition by plants, see Goodall and Filipowicz (1989) Cell 58, 473; Hanley and Schuler (1988) NAR 16, 159), is longer than about 70–73 bp (Goodall and Filipowicz (1990) Plant Mol. Biol. 14, 727), and is positioned close to the 5' end of the encoded mRNA, particularly in any untranslated leader sequence.

Cells of a plant can be transformed with the foreign DNA sequence of this invention in a conventional manner. Where the plant to be transformed is susceptible to Agrobacterium infection, it is preferred to use a vector, containing the foreign DNA sequence, which is a disarmed Ti-plasmid. The transformation can be carried out using procedures described, for example, in EP 0,116,718 and EP 0,270,822 and Gould et al (1991) Plant Physiology 95, 426–434. Preferred Ti-plasmid vectors contain the foreign DNA sequence between the border sequences or at least located upstream of the right border sequence. Of course, other types of vectors can be used for transforming the plant cell, using procedures such as direct gene transfer (as described for example in EP 0,223,247), pollen mediated transformation (as described for example in EP 0,270,356, PCT publication WO 85/01856 and EP 0,275,069), in vitro protoplast transformation (as described for example in U.S. Pat. No. 4,684,611), plant virus-mediated transformation (as described for example in EP 0,067,553 and U.S. Pat. No. 4,407,956) and liposome-mediated transformation (as described for example in U.S. Pat. No. 4,536,475).

Where the plant to be transformed is rice, recently developed transformation methods can be used such as the methods described for certain lines of rice by Christou et al (1991) Bio/Technology 9, 957, Lee et al (1991) PNAS 88, 6389, Shimamoto et al (1990) Nature 338, 274 and Datta et al (1990) Bio/Technology 8, 736.

Where the plant to be transformed is corn, recently developed transformation methods can be used such as the methods described for certain lines of corn by Fromm et al (1990) Bio/Technology 8, 833 and Gordon-Kamm et (1990) The Plant Cell 2, 603.

Where the plant to be transformed is wheat, a method analogous to those described above for corn or rice can be used. Preferably, for the transformation of a monocotyledonous plant, particularly a cereal such as rice, corn, or wheat, a method of direct DNA transfer, such as a method of biolistic transformation or electroporation, is used. When using such a direct transfer method, it is preferred to minimize the DNA that is transferred so that essentially only the foreign DNA sequence of this invention, with its male-sterility or fertility-restorer DNA and any marker DNA, is integrated into the plant genome. In this regard, when a foreign DNA sequence of this invention is constructed and multiplied on a plasmid in a bacterial host organism, it is preferred that, prior to transformation of a plant with the foreign DNA sequence, plasmid sequences that are required for propagation in the bacterial host organism, such as an origin of replication, an antibiotic resistance gene for selection of the host organism, etc., be separated from the parts of the plasmid that contain the foreign DNA sequence.

The Examples, which follow, describe: the isolation and the characterization of the rice cDNA sequences of SEQ ID nos. 1 to 5 of this invention; their use for isolating, from the rice genome, the stamen-specific promoters of this invention, such as the promoter PT72 upstream from nucleotide 2846 of SEQ ID no. 6, the promoter PT42 upstream from nucleotide 1809 of SEQ ID no. 7, and the promoter PE1 upstream from nucleotide 2264 of SEQ ID no. 8; the construction of gene cassettes by the fusion of each of these promoters with male-sterility and fertility-restorer DNAs; the construction of plant transformation vectors from the promoter cassettes; and the transformation of rice, corn and tobacco with the resulting plant transformation vectors.

Unless stated otherwise in the Examples, all procedures for making and manipulating recombinant DNA were carried out by the standard procedures described in Maniatis et al, *Molecular Cloning—A Laboratory Manual*, Cold Spring Harbor Laboratory Press, N. Y. (1982), as well as Sambrook et al, *Molecular Cloning—A Laboratory Manual, Second Edition*, Cold Spring Harbor Laboratory Press, N. Y. (1989). When making plasmid constructions, the orientation and integrity of cloned fragments were checked by means of restriction mapping and/or sequencing.

The sequence identification numbers referred to above and in the Examples are listed below.

Sequence Listing

SEQ ID no. 1: cDNA sequence of the T72 gene.

SEQ ID no. 2: partial cDNA sequence of the T23 gene.

SEQ ID no. 3: cDNA sequence of the T42 gene.

SEQ ID no. 4: cDNA sequence of the T155 gene.

SEQ ID no. 5: cDNA sequence of the E1 gene.

SEQ ID no. 6: DNA sequence of rice genomic clone hybridizing to T72 cDNA.

SEQ ID no. 7: DNA sequence of rice genomic clone hybridizing to T42 cDNA.

SEQ ID no. 8: DNA sequence of rice genomic clone hybridizing to E1 cDNA.

SEQ ID no. 9: DNA sequence of plasmid pVE108.

EXAMPLE 1

Isolation and characterization of anther-specific cDMAs from rice.

For the cloning of cDNAs corresponding to genes which are expressed exclusively, or at least predominantly, in anthers of rice, a cDNA library was prepared from poly $A^+$ mRNA isolated from immature spikelets (size 1–3 mm), at their developmental stages of carrying microsporocytes before meiosis and in early meiosis, and from anthers isolated from spikelets (size 3–5 mm), at their developmental stages of carrying microsporocytes undergoing meiosis and after meiosis, from the publicly available rice line *Oryza sativa* vat. *japonica*, Akihikari. By means of the Amersham cDNA Synthesis System Plus RPN 1256 Y/Z kit (Amersham International PLC, Buckinghamshire, England), cDNAs were synthesized using reverse transcriptase and an oligo dT primer, according to the directions set forth in the kit for its use.

The cDNAs were cloned in lambda gt10 vector, using the Amersham cDNA Cloning System—lambda gt10—RPN1257—kit, in accordance to the directions set forth in the kit for its use. Upon the cDNA libraries thus obtained (21,000 plaques for the anther library; 6,000 plaques for the spikelet library), differential screening was performed by hybridization with: a labelled first strand cDNA probe copied from rice immature anther mRNA and a labelled first strand cDNA probe copied from rice immature spikelet mRNA (developmental stages as above) as positive probes; and a labelled first strand cDNA probe copied from rice seedling leaf and a labelled first strand cDNA probe copied from rice seedling root as negative probes. 97 candidate anther- and spikelet-specific cDNA clones were selected and again screened with labeled cDNA probes derived from mRNA of anthers and spikelets of rice. (positive probes) and from leaf, root and basis of spikelets of rice (negative probes). The basis of spikelets are immature rice spikelets (size 3–6 mm) from which the anthers and the top of palea and lemma have been dissected away but which contain intact ovaries. 0.2 μg phage DNA from the 82 candidate clones passing this second selection step was screened for anther-specific expression in a dot blot assay, hybridized with: labelled first strand DNA probes copied from rice immature spikelet mRNA and rice immature anther mRNA (developmental stages as above) as positive probes; and labelled first strand cDNA probe copied from mRNA of rice seedling leaf, rice seedling root, basis of rice spikelet, dry rice seed, rice callus, and axis of immature rice panicle as negative probes (see Table 1). Thus, cDNA clones were identified which hybridize with at least one of the positive probes but for which no hybridization above background was detected with any of the negative probes.

cDNA inserts of 82 candidate clones were purified and hybridized with the collection of 82 candidate clones in order to identify cross-hybridizing and/or overlapping clones- This led to the identification of twenty two anther-specific cDNA clones which show no mutual cross-hybridization and thus are likely to be derived from different genes. Twenty of these clones were shown to correspond to single copy genes in the rice genome (as tested by Southern hybridization; see Table 1) and were subcloned in pGEM2 or pGEM7Zf(+) (PROMEGA, Madison, Wis., USA). 0.2 μg plasmid DNA from the twenty candidate clones was again screened for anther-specific expression in a dot blot assay as described above. Further analysis showed that there were actually only eighteen different inserts, and these inserts were hybridized to Northern blots with 5 μg total RNA from rice immature anther, immature spikelet, leaf and root. It was confirmed that sixteen out of eighteen clones tested are expressed in rice immature anther and immature spikelet (development stages as above) but not in leaf and root. The profiles of twelve of these selected differential clones, for which a partial or whole sequence was determined, are shown in Tables 1A, 1B and 1C. The twelve cloned anther-specific cDNA inserts were called "T146", "E1", "E2", "T34", "T72", "T157", "T149", "T42", "T139", "T155", "T23", and "T118". Five of these anther-specific cDNAs, i.e., the E1, T72, T42, T155 and T23 cDNAs, were further shown to be expressed both before and after meiosis of microsporocytes and also to exhibit strict anther-specific expression in a more sensitive analysis. The best expression level before meiosis was observed for the E1, T72, and T42 cDNAs. Of these three cDNAs, the T72 cDNA seemed to combine best the desired properties of anther specificity, relatively high level of expression, and substantial premeiotic expression.

The partial or whole sequences of the T72, T23, T42, T155 and E1 cDNAs, cloned in the pGEM plasmids, are shown in SEQ ID no. 1, SEQ ID no. 2, SEQ ID no. 3, SEQ ID no. 4, and SEQ ID no. 5, respectively. The cDNA sequence of T72 reveals two open reading frames (ORF) over 330 and over 114 nucleotides.

EXAMPLE 2

Isolation of the anther-specific genes corresponding to the anther-specific cDNA clones of Example 1 and identification of their anther-specific promoter regions To isolate the genomic DNA clones carrying the regulatory sequences of the T72, T23, T42, T155 and E1 genes, corresponding to the selected T72, T23, T42, T155 and E1 cDNAs of Example 1 cloned in the pGEM plasmids pT72, pT23, pT42, pT155 and pE1, respectively, a genomic library of rice var. Akihikari was constructed. This was done by partially digesting Akihikari seedling leaf DNA with Sau3AI, purifying the 18–22 kb size fraction by a sucrose gradient centrifugation, and cloning in the bacteriophage lambda EMBL3 replacement vector (as described by Frischauff et al (1983) J. Mol. Biol. 170, 827 and in Pouwels et al (1988) Cloning Vectors—A Laboratory Manual (Supplementary Update), Elsevier Science Publishers, Amsterdam) cleaved with BamHI and EcoRI. The library was screened with each of the whole pT72, pT23, pT42, pT155 and pE1 cDNA clones, and the restriction maps of the corresponding genomic clones were determined.

Corresponding genomic clones which hybridize to pT72, pT23, pT42, pT155 or pE1 are sequenced (Maxam and Gilbert (1977) PNAS 74, 560). Comparison of the sequences of pT72, pT23, pT42, pT155 or pE1 and the genomic clones leads to the identification of the homologous regions. For each of the five genes (T72, T23, T42, T155 and E1), the transcription initiation site is determined by primer extension using reverse transcriptase on mRNA of a rice tissue expressing the gene. A "TATA" consensus sequence box is found upstream of the transcription initiation site in the promoter of each of the five genes. The ATG translation initiation site is determined as the most upstream ATG codon in the translational reading frame of each clone, determined by DNA sequencing, and as the first accessible ATG codon on the mRNA synthesized in rice.

DNA sequences of parts of the genomic clones GT72, GT42 and GE1, hybridizing to pT72, pT42 and pE1 respectively, are shown in SEQ ID no. 6, SEQ ID no. 7 and SEQ ID no. 8 respectively. For each sequence, the TATA box and the transcription initiation site is indicated. In each sequence, a reading frame is identified that starts with an ATG translation initiation codon and that overlaps its corresponding cDNA sequence. The promoter region in each sequence is upstream from, and starts just before, the ATG translation initiation codon of the coding sequence. In this regard, the DNA starting from nucleotide I and ending with the nucleotide just before the ATG codon can be considered as the promoter region of each sequence. However, it appears that a preferred portion of each promoter region, for providing anther-specific expression of a heterologous coding sequence of interest (such as a sequence coding for barnase or RNase T1), extends only about 1500 to 1700 bp upstream from its ATG codon, and an even smaller portion of each promoter region extending only about 300 to 500 nucleotides upstream from its ATG codon is sufficient for providing anther-specific expression of a heterologous coding sequence. In each promoter region, the untranslated leader sequence, located between the transcription initiation site and the ATG start of translation, is preferred but is not considered essential for the anther-specific expression of a heterologous coding sequence, and the leader sequence can be replaced by the untranslated leader sequences of other genes, such as plant genes.

A 20 kbp genomic Sau3AI fragment was found that hybridized to the cDNA, pT72. A 4.6 kbp EcoRI fragment of this clone, which hybridized to the cDNA, pT72, was subcloned in pGEM2, and the resulting plasmid was designated "pGT72". A total of 3672 bp, upstream from the EcoRI site closest to the 3' end of the region of homology with the pT72 cDNA, was sequenced, and this sequence is shown in SEQ ID no. 6. By means of primer extension, the initiation of transcription was found to be at position 2765 of this sequence. The TATA box is presumed to be located between positions 2733 and 2739, while the translation initiation codon is located at position 2846. The sequence upstream of position 2846 can be used as a promoter region, PT72, for the anther-specific, particularly tapetum-specific, expression of a coding sequence of interest. A preferred portion of this promoter region appears to extend from about position 1242 to about position 2845, but the promoter region can comprise the entire sequence between positions 1 and 2845. It also appears that the minimum region which can serve as an anther-specific promoter extends about 300 to 500 bp upstream from position 2846 in SEQ ID no. 6.

Similarly, a genomic Sau3AI fragment (also of about 20 kbp in length) was recovered that hybridized to the cDNA, pT42. A 5 kbp HindIII fragment of this clone, which hybridized to the cDNA, pT42, was subcloned in pGEM2, and the resulting plasmid was designated as "pGT42". A total of 2370 bp, upstream from the HindIII site located within the region of homology with the pT42 cDNA, was sequenced, and this sequence is shown in SEQ ID no. 7. By means of primer extension, the initiation of transcription was found to be at position 1780 of this sequence. The TATA box is presumed to be located between positions 1748 and 1755, while the translation initiation codon is located at position 1809. The sequence upstream of position 1809 can be used as a promoter region, PT42, for the anther-specific, particularly tapetum-specific, expression of a coding sequence of interest. A preferred portion of this promoter region appears to extend from about position 275 to about position 1808, but the promoter region can comprise the entire sequence between positions 1 and 1808. It also appears that the minimum region which can serve as an anther-specific promoter extends about 300 to 500 bp upstream from position 1809 in SEQ ID no. 7.

Similarly, a genomic Sau3AI fragment (also of about 20 kb in length) was recovered that hybridized to the cDNA, pE1. A 6 kbp PvuII fragment of this clone, which hybridized to the cDNA, pE1, was subcloned in the SmaI site of pGEM2, and the resulting plasmid was designated as "pGE1". A total of 2407 bp, upstream from the PvuII site located within the region of homology with the pE1 cDNA, was sequenced, and this sequence is given in SEQ ID no. 8. By means of primer extension, the initiation of transcription was found to be at position 2211 of this sequence. The TATA box is presumed to be located between positions 2181 and 2187, while the translation initiation codon is located at position 2264. The sequence upstream of position 2264 can be used as a promoter region, PE1, for the anther-specific, particularly tapetum-specific, expression of a coding sequence of interest. A preferred portion of this promoter region appears to extend from about position 572 to about position 2263, but the promoter region can comprise the entire sequence between positions 1 and 2263. It appears also that the minimum region which can serve as an anther-specific promoter extends about 300 to 500 bp upstream from position 2264 in SEQ ID no. 8.

EXAMPLE 3

Construction of promoter cassettes derived from the anther-specific promoter regions of Example 2

The 5' regulatory sequences, including the promoter, of each of the five anther-specific genes of Example 2 are subcloned into the polylinker of pMAC 5-8 (EPA 87402348.4). This produces vectors which can be used to isolate single stranded DNAs for use in site-directed mutagenesis reactions. Using site-directed mutagenesis (EPA 87402348.4), sequences surrounding the ATG translation initiation codon of the 5' regulatory sequences of each of the anther-specific genes are modified to create a unique recognition site for a restriction enzyme for which there is a corresponding recognition site at the 5' end of each of the male-sterility and fertility-restorer DNAs (that are to be fused to the 5' regulatory sequences in Example 4, below). Each of the resulting plasmids contains the newly created restriction site. The precise nucleotide sequence spanning each newly created restriction site is determined in order to confirm that it only differs from the 5' regulatory sequences of the corresponding rice anther-specific gene by the substitution, creating the new restriction site.

EXAMPLE 4

Construction of plant transformation vectors from the promoter cassettes of Example 3 and from the anther-specific promoter regions of Example 2

Using the procedures described in EPA 89401194.9 and 90402281.1, the promoter cassettes of Example 3 are used to construct plant transformation vectors comprising foreign chimaeric DNA sequences of this invention, each of which contains the 5' regulatory sequences, including one of the anther-specific promoters, corresponding to each of the five anther-specific genes isolated in Example 2. The 5' regulatory sequences are upstream of, are in the same transcriptional unit as, and control either a male-sterility DNA (from EPA 89401194.9) encoding barnase from *Bacillus amyloliquefaciens* (Hartley and Rogerson (1972) Preparative Biochemistry 2 (3), 243–250) or a fertility-restorer DNA (from EPA 90402281.1) encoding barstar (Hartley and Rogerson (1972) supra; Hartley and Sweaton (1973) J. Biol. Chem. 248 (16), 5624–5626). Downstream of each male-sterility or fertility-restorer DNA is the 3' end of the nopaline synthase gene (An et al (1985) EMBO J. 4 (2), 277). Each chimaeric DNA sequence also comprises the 35S3 promoter (Hull and Howell (1987) Virology 86, 482–493) fused in frame with the sfr gene encoding phosphinothricine resistance (EPA 87400544.0) and the 3' end signal of the T-DNA gone 7 (Velten and Schell (1985) NAR 13, 6987).

EXAMPLE 5

Construction of plant transformation vectors containing the barstar gene under the control of the taperum-specific promoters of Example 2

Suitable vectors, which carry both the barstar-encoding DNA (Hartley and Rogerson (1972), supra) under the control of the tapetum-specific PT72 promoter of this invention (Example 2) and the herbicide resistance gene, bar (EP 0,242,236), under the control of the 35S3 promoter (EP 0,359,617) and which can be used for the transformation of rice (in Example 7) and corn (in Example 8), are constructed in a procedure comprising four steps as outlined below. Plasmid pVE108, the sequence of which is shown in SEQ ID no. 9, is used.

Step 1.

A DNA fragment, carrying the 3' untranslated end of the nos gene of Agrobacterium T-DNA, is amplified from pVE108 by means of the polymerase chain reaction (PCR; Sambrook et al (1989) supra) using the following two oligonucleotides (CASOL3 and CASOL4) as primers:

| | |
|---|---|
| CASOL3: | 5'-TGG CCA TGG AGG GTA ACC TCC GAA GCA GAT CGT TCA-3' (SEQ ID NO: 10) |
| CASOL4: | 5'-CGA ATT CAT ATG CAC GTG TTC CCG ATC TAG TAA CAT-3' (SEQ ID NO: 11). |

The resulting fragment is recovered, cleaved with EcoRI and NcoI, and ligated to the large fragment of plasmid pVE108 cleaved with the same enzymes, yielding plasmid pTSX11.

Step 2.

A fragment containing a tapetum-specific promoter PT72 and a barstar gene is constructed as follows:

1) a DNA fragment, carrying the barstar coding sequence, is amplified from pMT416 (Hartley (1988) J. Mol. Biol. 202, 913) by means of PCR using the following two oligonucleotides (CASOL13T72 and CASOL14) as primers:

| | |
|---|---|
| CASOL13T72: | CGG CAG AAG ACA CTC ACG GCG ATG AAA AAA GCA GTC ATT AAC-3' (SEQ ID NO: 12) |
| CASOL14: | 5'-GGG GGT TAC CTT AAG AAA GTA TGA TGG TGA-3' (SEQ ID NO: 13); and |

2) a DNA fragment, carrying the barstar coding sequence under the control of the PT72 promoter of Example 2, is amplified from pT72 (Example 2) by means of PCR using as primers: i) the gel-purified PCR product of step 1), ii) CASOL14, and iii) the following oligonucleotide (T72POL1):

5'-TGG CCA TGG AGC TAG CGG CCG CCA CAG AAC AGG ATA GCA A-3' (SEQ ID NO: 14).

The final fragment contains not only the barstar coding sequence under the control of the PT72 promoter but also comprises: at its 5' end, a linker sequence containing restriction sites for MscI, NcoI, NheI and NotI; and at its 3' end, a linker sequence comprising a BstEII restriction site and a 3 nucleotide spacer (GGG).

Step 3.

The final fragment of Step 2 is recovered, cleaved with NcoI and BstEII, and ligated to the large fragment of plasmid pTSXll (Step 1) cleaved with the same enzymes, yielding plasmid pTSX11-T72.

Step 4.

A fragment containing the 35S3 promoter is amplified from pDE9 (EP 0,359,617) by means of PCR using the following two oligonucleotides as primers:

5'-TGG CCA TGG TTA TAG AGA GAG AGA TAG ATT T-3' (SEQ ID NO: 15)
5'-GAA GCT AGC AAT CCC ACC AAA ACC TGA ACC T-3' (SEQ ID NO: 16).

The resulting fragment is recovered, cleaved with NcoI and NheI, and ligated to the large fragment of pTSX11-T72 (Step 3) cleaved with the same enzymes, yielding the plasmid designated as "pJVR1-T72".

For constructions with the PE1 promoter instead of the PT72 promoter, the four step procedure, described above, is followed except that in step 2 the following two oligonucleotides (CASOL13E1 and E1POL1) are used instead of CASOL13T72 and T72POL1 respectively:

| | |
|---|---|
| CASOL13E1: | GAG ATC CAT CAA GCC GTC GCG ATG AAA AAA GCA GTC ATT AAC-3' (SEQ ID NO: 17) |
| E1POL1: | 5'-TGG CCA TGG AGC TAG CGG CCG CAG ATC CTT CTG TGT GAT TG-3' (SEQ ID NO: 18). |

The plasmid obtained after step 3 is designated as "pTSX11-E1" while the plasmid obtained after Step 4 is designated as "pJVR1-E1".

For constructions with the PT42 promoter instead of the PT72 promoter, the four step procedure, described above, is used except that:

1) in step 2, the following two oligonucleotides (CASOL13T42 and T42POL1) are used instead of CASOL13T72 and T72POL1 respectively:

| | |
|---|---|
| CASOL13T42: | 5'-CAA CTC CCC TCC TCC ACT AGA CCA CCA TGA AAA AAG CAG TCA TTA AC-3' (SEQ ID NO: 19) |
| T42POL1: | 5'-GCT AGC GGC CGC ATG GCA GAG CAC GGC CAG-3' (SEQ ID NO: 20); |

2) the fragment obtained in step 2 is inserted in pTSX11 (Step 3) as follows: the fragment is made blunt end with Klenow and cleaved with BstEII and is then ligated to the large fragment of pTSX11 cleaved with NcoI (filled-in with Klenow) and BstEII. The resulting plasmid is designated as "pTSX11-T42"; and 3) the NotI-HindIII fragment of pJVR1-T72, carrying the bar gene under the control of the 35S3 promoter, is ligated to the large fragment of pTSX11-T42 cleaved with the same enzymes. The plasmid obtained is designated as "pJVR1-T42".

Alternative constructions are also made starting from plasmid pUCNew1 (Example 6). The barstar encoding DNA present on pUCNew1 is first removed by digestion with XhoI and religation, yielding plasmid pUCNew2. The EcoRI-HindIII fragments from pJVR1-T72, pJVR1-E1 and pJVR1-T42, each carrying the barstar-encoding DNA under the control of a rice anther-specific promoter and the bar gene under the control of the 35S3 promoter, are then inserted in the EcoRI and HindIII sites of pUCNew2, yielding pJVR3-T72, pJVR3-E1, pJVR3-T42 respectively.

Plasmids pJVR3-T72, pJVR3-E1, pJVR3-T42, pJVR1-T72, pJVR1-E1, pJVR1-T42 are used for the transformation of rice and corn as described in Examples 7 and 8, respectively.

T-DNA vectors for Agrobacterium-mediated plant transformations are prepared by cloning the appropriate EcoRI (filled-in with Klenow)—HindIII fragments of pJVR1-T72, pJVR1-E1, and pJVR1-T42 (containing the 35S3-bar and rice anther-specific promoter-barnase chimaeric genes) between the HindIII and XbaI (filled-in with Klenow) sites of the known T-DNA vectors pGSC1700 or pGSC1701A. pGSC1700 has been deposited on Mar. 21, 1988 at the Deutsche Sammlung für Mikroorganismen und Zellkulturen (DSM), Mascheroderweg 1B, D-330 Braunschweig, Germany under DSM accession number 4469, and pGSC1701A has been deposited on Oct. 22, 1987 at the DSM under DSM accession number 4286. The T-DNA vectors are used for transformation of tobacco as described in Example 9.

EXAMPLE 6

Construction of plant transformation vectors containing the barnase gene under the control of the tapetum-specific promoters of Example 2

The tapetum-specific PT72, PT42 and PTE1 promoters of Example 2 are also directly cloned in plant transformation vectors containing the barnase-encoding male-sterility DNA and barstar-encoding fertility-restorer DNA of Example 4. Plasmid pVE108, the sequence of which is shown in SEQ ID no. 9, is used. The plasmid contains a chimaeric gene comprising: the bar gene (EP 0,242,236) under the control of the 35S3 promoter (EP 0,359,617) and with the 3' regulatory sequence of the nopaline synthase gene: and the barnase gene under the control of the taperum-specific promoter of the TA29 gene (EP 0,344,029) of Nicotiana tabacum and with the 3' regulatory sequence of the nopaline synthase gene. For constitutive expression of the bar gene, an equivalent 35S3 promoter also is used, which differs from the one described in EP 0,359,617 by a 550 bp EcoRI-StuI deletion.

The large NcoI fragment of plasmid pVE108 (filled-in with the large fragment—Klenow—of DNA polymerase I of E. coli) is first ligated to the fragment of the 35S3 promoter as described in EP 0,359,617, amplified by means of the polymerase chain reaction (PCR) using 5'-ATT ATA GAG AGA GAG ATA GAT TT-3' (SEQ ID NO: 21)
5'-GCA ATC CCA CCA AAA CCT GAA CCT-3' (SEQ ID NO: 22).

The plasmid, in which the NcoI site is reconstructed at the ATG translation initiation codon of the barnase gene, is designated "pVE108del". In this plasmid, the NcoI site at the ATG translation initiation codon of the bar gene is lost.

Then, pVE108del is digested with NcoI, filled in with Klenow, and ligated to one of the following DNA fragments:

1. a 1602 bp fragment obtained by PCR amplification from pGT72 using the following primers:

5'-ATT CCA CAG AAC AGG ATA GC-3' (SEQ ID NO: 23)
5'-GCC GTG AGT GTC TTC TGC CG-3' (SEQ ID NO: 24).

The resulting plasmid, in which the promoter fragment from pGT72 is appropriately positioned with respect to the barnase coding sequence, is designated "pVE108-T72";

2. a 1532 bp fragment obtained by PCR amplification from pGT42 using the following primers:

5'-CCA TGG CAG AGC ACG GCC AG-3' (SEQ ID NO: 25)
5'-GTG GTC TAG TGG AGG AGG GGA GTT G-3' (SEQ ID NO: 26).

The resulting plasmid, in which the promoter fragment from pGT42 is appropriately positioned with respect to the barnase coding sequence, is designated "pVE108-T42"; and 3. a 1690 bp fragment obtained by PCR amplification from pGE1 using the following primers:

5'-CCT CAG ATC CTT CTG TGT GA-3' (SEQ ID NO: 27)
5'-GCG ACG GCT TGA TGG ATC TCT TGC-3' (SEQ ID NO: 28).

The resulting plasmid, in which the promoter fragment from pGT72 is appropriately positioned with respect to the barnase coding sequence, is designated "pVE108-E1".

Alternatively, plasmids pVE108-T72, pVE108-T42 and pVE108-E1 are obtained directly by cloning, in pVE108del, their corresponding promoter fragments obtained by direct PCR amplification from rice genomic DNA using the above-mentioned primers of this Example.

Alternatively, suitable vectors, which carry both the barnase-encoding DNA under the control of the tapetum-specific PT72, PTE1 or PT42 promoter of this invention (Example 2) and the bar gene under the control of the 35S3 promoter and which can be used for transformation of rice (Example 7) and corn (Example 8), are constructed by the four step procedure of Example 5. However, the oligonucleotides used in Step 2 are complementary to the barnase gene in pMT416 instead of to the barstar gene. In this regard, CASOL13T72 is replaced by CASOL15T72, CASOL13T42 is replaced by CASOL15T42, CASOL13E1 is replaced by CASOL15E1, and CASOL14 is replaced by CASOL16. These replacement oligonucleotides are as follows:

| | |
|---|---|
| CASOL15T72: | 5'-CGG CAG AAG ACA CTC ACG GCG ATG GTA CCG GTT ATC AAC ACG-3' (SEQ ID NO: 29) |
| CASOL15T42: | 5'-CAA CTC CCC TCC TCC ACT AGA CCA CCA TGG TAC CGG TTA TCA ACA CG-3' (SEQ ID NO: 30) |
| CASOL15E1: | 5'-GAG ATC CAT CAA GCC GTC GCG ATG GTA CCG GTT ATC AAC ACG-3' (SEQ ID NO:31) |
| CASOL16: | 5'-GGG GGT TAC CTT ATC TGA TTT TTG TAA AGG TCT G-3' (SEQ ID NO: 32). |

The final constructions obtained after step 4 are designated as "pJVR2-T72", "pJVR2-E1" and "pJVR2-T42" respectively.

All vector constructions, containing the barnase-encoding DNA are made in plasmid pMc5-BS in *E. coli* WK6. Plasmid pMc5-BS contains the barstar-encoding DNA gene under the control of the tac promoter (De Boer et al (1983) PNAS 80, 21) and is constructed by cloning the EcoRI-HindIII fragment of pMT416 (Hartley (1988) J. Mol. Biol. 202, 913) into pMc5-8 (deposited on May 3, 1988 at the DSM under DSM accession number 4566). The sequence starting with the PhoA signal sequence and ending with the last nucleotide before the translation initiation codon of the barstar-coding region is deleted by looping-out mutagenesis according to the general procedures described by Sollazi et al (1985) Gene 37, 199. The availability of an ampicillin resistance gene on the pUCIS-derived plasmids carrying the chimaeric barnase-coding sequence and the chloramphenicol resistance gene on pMc5-BS permits the strain to be kept stable on plates provided with the two antibiotics or to select for any one plasmid. While normally repressed, gene expression from this promoter can be induced by the addition of a commonly used inducer of the lac operon, IPTG (isopropyl-β-d-thiogalactopyranoside).

Alternatively the barstar-encoding DNA under the control of the tac promoter is inserted in the same plasmid as that carrying the barnase-encoding DNA under the control of a rice anther-specific promoter of this invention as follows.

In a first step, a new plasmid is constructed by ligation of the three following DNA fragments:

A DNA fragment, comprising the β-lactamase gene from pUC19 (Yanisch-Perron et al (1985) Gene 33, 103), is amplified from pUC19 by means of PCR using the following two oligonucleotides (CASOL9 and CASOL11):

the control of the tac promoter inserted between the β-lactamase gene and the origin of replication of PUC19 (with the barstar-encoding DNA in the same orientation as the β-lactamase gene), is designated as "pUCNew1". The EcoRI-HindIII fragments from pJVR2-T72, pJVR2-E1 and pJVR2-T42, each carrying the barnase-encoding DNA under the control of one of the rice anther-specific promoters of this invention and the bar gene under the control of the 35S3 promoter, are then each inserted in the EcoRI and HindIII sites of pUCNew1, yielding pJVR4-T72, pJVR4-E1 and pJVR4-T42 respectively.

Plasmids pVE108-T72, pVE108-T42, pVE108-E1, pJVR2-T72, pJVR2-T42, pJVR2-E1, pJVR4-T72, pJVR4-T42 and pJVR4-E1 are each used for transformation of rice and corn as described in Examples 7 and 8, respectively.

T-DNA vectors for Agrobacterium-mediated plant transformations are prepared by cloning the appropriate EcoRI (filled-in with Klenow)—XbaI fragments of pVE108-T72, pVE108-T42, pVE108-E1, pJVR2-T72, pJVR2-T42, pJVR2-E1, pJVR4-T72, pJVR4-T42 and pJVR4-E1 (containing the 35S3-bar and rice anther-specific promoter-barnase chimaeric genes) between the HindIII (filled-in with Klenow) and XbaI sites of the known T-DNA vectors, pGSC1700 (DSM 4469) or pGSC1701A (DSM 4286). The T-DNA vectors are used for transformation of tobacco as described in Example 9.

EXAMPLE 7

Transformation of rice with the plant transformation vectors from Examples 5 and 6

Using the procedures described by Datta et al (1990) supra, protoplasts of the rice line, *Oryza sativa* var. Chinsurah boro II, are transformed with the plant transformation vectors described in Examples 5 and 6, and transformed plants are regenerated from the protoplasts.

| | |
|---|---|
| CASOL 9: | 5'-GGA ATT CAA GCT TGA CGT CAG GTG GCA CTT-3' (SEQ ID NO: 33) |
| CASOL11: | 5'-TGG GGA GTA AGC TCG AGC CAA AAA GGA TCT TCA CCT AG-3' (SEQ ID NO: 34).<br>Another DNA fragment, comprising the origin of replication of pUC19, is amplified from pUC19, by means of PCR using the following two oligonucleotides (CASOL10 and CASOL12): |
| CASOL10: | 5'-GGA ATT CTG ATC AGG CCA ACG CGC GGG GAG A-3' (SEQ ID NO: 35) |
| CASOL12: | 5'-TCT TAA TAC GAT CAA TGG CTC GAG TCT CAT GAC CAA AAT CCC TTA-3' (SEQ ID NO: 36).<br>Yet another DNA fragment, comprising the barstar-encoding DNA under the control of the tac promoter, is amplified from pMc5-BS by means of PCR using the following two oligonucleotides (CASOL17 and CASOL18): |
| CASOL17: | 5'-CGG CTC GAG CTT ACT CCC CAT-3' (SEQ ID NO: 37) |
| CASOL18: | 5'-CCG CTC GAG CCA TTG ATC GTA TTA AGA-3' (SEQ ID NO: 38). |

These three DNA fragments are then cleaved with XhoI and EcoRI and ligated to one another. The resulting plasmid, which resembles pUC19 but which has a deleted lac region, an altered polylinker, and the barstar-encoding DNA under Alternatively, immature embryos from rice varieties Gulfmont, Lemont, IR26, IR 36, IR54, and IR72 are bombarded with gold particles, carrying appropriate plasmid DNA of Examples 5 and 6, and transformed plants are regenerated from the embryos by the procedures described by Christou et al (1991) Bio/Technology 9, 957. In this regard, transformations with male-sterility DNAs and male fertility-restorer DNAs are carried out using pJVR2-T72, pJVR2-E1, pJVR2-T42, pVE108-T72, pVE108-E1, pVE108-T42, pJVR1-T72, pJVR1-E1, and pJVR1-T42 (Examples 5 and 6), either directly or following suitable linearization after the PT72- and PT42-containing plasmids are digested with EcoRI and HindIII and the PE1-containing plasmids are digested with EcoRI and PstI. These transformations are also carried out with foreign DNA sequences of this invention containing only a male-sterility DNA or a fertility-restorer DNA and a selectable marker DNA, using pJVR4-T72, pJVR4-E1, pJVR4-T42, pJVR3-T72, pJVR3-E1, and pJVR3-T42 (Examples 5 and 6), after being digested with EcoRI and XhoI and then size fractionated by agarose gel electrophoresis or by sucrose gradient centrifugation, so that each foreign DNA sequence can be recovered, digested with XhoI, after which: the fragments are filled-in in a reaction with T4 DNA polymerase, dATP, dCTP, dGTP and biotin-dUTP; and after heat inactivation of the enzymes, the DNA is further digested with EcoRI, and the biotinylated XhoI ends are removed on a streptavidin agarose column (Sigma) or on streptavidin magnetic beads (Promega).

Each transformed plant, containing the tapetum-specific PT72, PT42 or PE1 promoter of Example 2 controlling either a male-sterility DNA or a fertility-restorer DNA, is normal except for its flowers. In this regard, each plant containing a male-sterility DNA under the control of a tapetum-specific promoter expresses such DNA at least predominantly in its tapetum cells and produces no normal pollen, and each plant containing a fertility-restorer DNA under the control of a tapetum-specific promoter expresses such DNA at least predominantly in its tapetum cells but produces normal pollen.

EXAMPLE 8

Transformation of corn with the plant transformation vectors from Examples 5 and 6

Using the procedures described by Fromm et al (1990) supraemhryogenic suspension cultures of a B73×A188 corn line are transformed with the plant transformation vectors described in Examples 5 and 6, and transformed plants are regenerated from the embryogenic suspension cultures. Alternatively, immature embryos from the B73×A188 corn line are transformed with gold particles carrying the plasmid DNA of Examples 5 and 6, and transformed plants are regenerated from the embryos as described in Example 7. Each transformed plant, containing the tapetum-specific PT72, PT42 or PE1 promoter of Example 2 controlling either a male-sterility DNA or a fertility-restorer DNA, is normal except for its flowers. In this regard, each plant containing a male-sterility DNA under the control of a tapetum-specific promoter expresses such DNA at least predominantly in its tapetum cells and produces no normal pollen, and each plant containing a fertility-restorer DNA under the control of a tapetum-specific promoter expresses such DNA at least predominantly in its taperum cells but produces normal pollen.

EXAMPLE 9

Transformation of tobacco with the plant transformation vectors from Examples 4, 5 and 6

Using the procedures described in EPA 89401194.9 and 90402281.1, tobacco plants are transformed by Agrobacterium-mediated transfer with the plant transformation vectors containing the foreign chimaeric DNA sequences from Examples 4, 5 and 6. The transformed tobacco plants, each containing one of the anther-specific promoters of Example 2 controlling either a male-sterility DNA or a fertility-restorer DNA, are normal except for their flowers. In this regard, each plant containing a male-sterility DNA under the control of an anther-specific promoter expresses such DNA at least predominantly in its anthers and produces no normal pollen, and each plant containing a male fertility-restorer DNA under the control of an anther-specific promoter expresses such DNA at least predominantly in its anthers but produces normal pollen.

Needless to say, the use of the anther-specific rice promoters of this invention is not limited to the transformation of any specific plant(s). The rice promoters can be useful in any crop where they are capable of controlling gene expression, and preferably where such expression is to occur at least predominantly, preferably specifically, in stamen cells of the crop. Also, the use of these promoters is not limited to the control of male-sterility DNAs or fertility-restorer DNAs but can be used to control the expression of any gene selectively in stamen cells.

Furthermore, this invention is not limited to the specific stamen-specific, preferably anther-specific, particularly tapetum-specific, promoters described in the foregoing Examples. Rather, this invention encompasses promoters equivalent to those of Example 2 which can be used to control the expression of a structural gene, such as a male-sterility DNA or a fertility-restorer DNA, selectively in stamen cells, preferably anther cells, particularly tapetum cells, of a plant. Indeed, it is believed that the DNA sequence of each of the promoters of Example 2 can be modified by replacing some of its nucleotides with other nucleotides, provided that such modifications do not alter substantially the ability of polymerase complexes, including transcription activators, of stamen cells, particularly anther cells, to recognize the promoter, as modified.

TABLE 1

PROFILES OF SELECTED DIFFERENTIAL CLONES
TABLE 1A

| name | cDNA size | mRNA size | copy number | dot blot assay for expression in RNA sample | | |
|---|---|---|---|---|---|---|
| | | | | anther | spikelet 1.5–3 mm | spikelet 4–6 mm |
| E1 | 530 | 800 | 1 | 8 | 7 | 7 |
| T72 | 400 | 800 | 1 | 9 | 7 | 9 |
| T157 | 600 | 1900 | 1 | 7 | 0 | 7 |
| T149 | 500 | 2600 | 1 | 7 | 2 | 8 |
| T42 | 270 | 800 | 1 | 8 | 7 | 6 |
| T146 | 1200 | | 1 | 4 | 1 | 5 |
| T139 | 200 | 1200 | 1 | 8 | 6 | 7 |
| T155 | 250 | 900 | 1 | 7 | 4 | 5 |
| T34 | 650 | 800 | 1 | 9 | 8 | 7 |
| T23 | 1000 | 1300 | 1 | 8 | 4 | 9 |
| T118 | 700 | 1100 | 1 | 5 | 7 | 5 |
| E2 | 700 | 800 | 1 | 6 | 6 | 5 |

TABLE 1B

| cDNA name | cDNA size | mRNA size | copy number | dot blot assay for expression in RNA sample | | | | | |
|---|---|---|---|---|---|---|---|---|---|
| | | | | leaf | root | 1 | 2a | 2b | 2c |
| E1 | 530 | 800 | 1 | 0 | 0 | 0 | 1 | 1 | 1 |
| T72 | 400 | 800 | 1 | 0 | 0 | 0 | 2 | 1 | 1 |
| T157 | 600 | 1900 | 1 | 0 | 1 | 0 | 1 | 1 | 1 |
| T149 | 500 | 2600 | 1 | 0 | 1 | 0 | 1 | 1 | 1 |
| T42 | 270 | 800 | 1 | 0 | 1 | 0 | 2 | 1 | 1 |
| T146 | 1200 | | 1 | 1 | 1 | 1 | 1 | 1 | 1 |
| T139 | 200 | 1200 | 1 | 1 | 0 | 0 | 2 | 2 | 1 |
| T155 | 250 | 900 | 1 | 1 | 1 | 1 | 1 | 1 | 1 |
| T34 | 650 | 800 | 1 | 2 | 2 | 1 | 2 | 2 | 2 |
| T23 | 1000 | 1300 | 1 | 2 | 1 | 2 | 2 | 2 | 2 |
| T118 | 700 | 1100 | 1 | 3 | 2 | 2 | 2 | 2 | 2 |
| E2 | 700 | 800 | 1 | 3 | 3 | 2 | 2 | 2 | 2 |

TABLE 1C

| cDNA name | cDNA size | mRNA size | copy number | dot blot assay for expression in RNA sample | | |
|---|---|---|---|---|---|---|
| | | | | dry seed | callus | axis |
| E1 | 530 | 800 | 1 | 0 | 0 | 0 |
| T72 | 400 | 800 | 1 | 0 | 0 | 0 |
| T157 | 600 | 1900 | 1 | 0 | 0 | 1 |
| T149 | 500 | 2600 | 1 | 0 | 0 | 1 |
| T42 | 270 | 800 | 1 | 0 | 0 | 0 |
| T146 | 1200 | | 1 | 0 | 1 | 1 |
| T139 | 200 | 1200 | 1 | 1 | 1 | 0 |
| T155 | 250 | 900 | 1 | 0 | 1 | 1 |
| T34 | 650 | 800 | 1 | 0 | 2 | 2 |
| T23 | 1000 | 1300 | 1 | 0 | 3 | 3 |
| T118 | 700 | 1100 | 1 | 0 | 3 | 3 |
| E2 | 700 | 800 | 1 | 0 | 4 | 3 | legend:

basis of spikelet subdivision:

1: "white" spikelets of 6–6.5 mm 2a, 2b, 2c: immature spikelets of 3–5 mm; the three categories correspond to different samples of mRNA from different batches of the same type of tissue (preparaions of basis of spikelets may have been contaminated with remnants of anthers)

1 to 9: corresponds to expression level; 0 corresponds to a hybridization level not higher than the background (hybridization obtained with pGEM2 without insert).

empty boxes: not determined mRNA size: has been determined by Northern blot copy number: corresponds to the number of hybridizing bands detected with the cDNA inserts as a probe in Southern blots of Akihikari leaf genomic DNA digested with a majority of restriction enzymes tested, (AvaI, BamHI, BglII, EcoRI, HindIII, KpnI, MspI, RsaI, and SacI).

We claim:

1. An isolated promoter region from a rice gene, wherein said rice gene is a single copy gene which encodes a mRNA that is produced selectively in stamen cells of a rice plant and is capable of hybridizing to a cDNA with a nucleotide sequence selected from the group consisting of: SEQ ID NO:1, SEQ ID NO:3, and SEQ ID NO:5, under conditions in which no other rice gene hybridizes to said cDNA; and
    wherein said promoter region comprises a DNA of about 300 to about 2900 bp in length that is located immediately upstream of the translation initiation codon of said rice gene.

2. The isolated promoter region of a rice gene according to claim 1, wherein said rice gene is capable of hybridizing to a cDNA with a nucleotide sequence selected from the group consisting of SEQ ID NO:1, SEQ ID NO:3 and SEQ ID NO:5;
    wherein said cDNA, when used as a probe hybridizes as one single band in Southern blots of digested rice leaf genomic DNA with a majority of restriction enzymes tested, wherein said restriction enzymes tested are AvaI, BamHI, BglII, EcoRI, HindIII, KpnI, MspI, RsaI and SacI.

3. The stamen-specific promoter region according to claim 1, which has a length of about 1500 to about 1700.

4. The stamen-specific promoter region according to claim 1, which comprises the nucleotide sequence starting between about nucleotide position 2345 and 2545 and ending at nucleotide position 2845 of SEQ ID NO:6.

5. The stamen-specific promoter region according to claim 4 which comprises the nucleotide sequence starting at about nucleotide position 1242 and ending at nucleotide position 2845 of SEQ ID NO:6.

6. The stamen-specific promoter region according to claim 4 which comprises the nucleotide sequence starting at about nucleotide position 1 and ending at nucleotide position 2845 of SEQ ID NO:6.

7. The stamen-specific promoter region according to claim 1 which comprises the nucleotide sequence starting between about nucleotide positions 1308 and 1508 and ending at nucleotide position 1808 of SEQ ID NO:7.

8. The stamen-specific promoter region according to claim 7 which comprises the nucleotide sequence starting at about nucleotide position 275 and ending at nucleotide position 1808 of SEQ ID NO:7.

9. The stamen-specific promoter region according to claim 7, which comprises the nucleotide sequence starting at about nucleotide position 1 and ending at nucleotide position 1808.

10. The stamen-specific promoter region according to claim 1, which comprises the nucleotide sequence starting between about nucleotide positions 1763 and 1963 and ending at nucleotide position 2263 of SEQ ID NO:8.

11. The stamen-specific promoter region according to claim 10, which comprises the nucleotide sequence starting at about position 572 and ending at nucleotide position 2263 of SEQ ID NO:8.

12. The stamen-specific promoter region according to claim 10, which comprises the nucleotide sequence starting at about nucleotide position 1 and ending at nucleotide position 2263 of SEQ ID NO:8.

13. The stamen-specific promoter region according to claim 1 in which the untranslated leader sequence is replaced by the untranslated leader sequence of another plant-expressible gene.

14. The stamen-specific promoter region according to claim 4 in which the untranslated leader sequence is replaced by the untranslated leader sequence of another plant-expressible gene.

15. The stamen-specific promoter region according to claim 7 in which the untranslated leader sequence is replaced by the untranslated leader sequence of another plant-expressible gene.

16. The stamen-specific promoter region according to claim 10 in which the untranslated leader sequence is replaced by the untranslated leader sequence of another plant-expressible gene.

17. A chimeric gene comprising the promoter region according to claim 1 and a heterologous sequence coding for a RNA, protein or polypeptide.

18. A chimeric gene according to claim 17 in which said heterologous sequence is a sequence encoding barnase or a sequence encoding barstar.

19. A plant cell containing the chimeric gene according to claim 17.

20. A plant cell containing the chimeric gene according to claim 18.

21. A plant or a plant seed containing the chimeric gene of claim 17.

22. A plant or a plant seed containing the chimeric gene according to claim 18.

23. A process for obtaining a promoter region from a single copy rice gene that encodes a mRNA selectively produced in stamen cells of rice plants, wherein said process comprises the following steps:
    (a) hybridizing the 18–22 kb size fraction of rice genomic DNA partially digested with Sau3A1 with a cDNA selected form the group consisting of: SEQ ID NO:1, SEQ ID NO:3, and SEQ ID NO:5; under conditions in which only a single DNA fragment of said size fraction hybridizes to said cDNA, and (b) obtaining said promoter region by isolating from said single DNA fragment the DNA of at least about 300 to 500 bp in length which is located immediately upstream of the translation initiation codon of the rice gene that hybridizes to said cDNA.

* * * * *

UNITED STATES PATENT AND TRADEMARK OFFICE
CERTIFICATE OF CORRECTION

PATENT NO. : 5,639,948

DATED : JUNE 17, 1997

INVENTOR(S) : MICHIELS ET AL.

It is certified that error appears in the above-identified patent and that said Letters Patent is hereby corrected as shown below:

Column 13, line 56, after "using" insert —the following two oligonucleotides as primers:—.

Column 15, line 26, "pUCIS" should read —pUC18—.

Column 53, line 40, "HindLIII" should read —HindIII—.

Column 53, line 43, after "1700" insert —bp—.

Column 54, line 67, "form" should read —from—.

Signed and Sealed this

Second Day of February, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 446 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: rice
        ( F ) TISSUE TYPE: anther ( i x ) FEATURE:
        ( A ) NAME/KEY: misc_feature
        ( B ) LOCATION: 1..21
        ( D ) OTHER INFORMATION: /product="cloning adaptor sequence"

( i x ) FEATURE:
        ( A ) NAME/KEY: misc_feature
        ( B ) LOCATION: 22..429
        ( D ) OTHER INFORMATION: /product="cDNA T72"

( i x ) FEATURE:
        ( A ) NAME/KEY: misc_feature
        ( B ) LOCATION: 430..446

( D ) OTHER INFORMATION: /product="cloning adaptor
                sequences"

( i x ) FEATURE:
            ( A ) NAME/KEY: misc_feature
            ( B ) LOCATION: 22..144
            ( D ) OTHER INFORMATION: /product="open reading framer"

( i x ) FEATURE:
            ( A ) NAME/KEY: misc_feature
            ( B ) LOCATION: 23..334
            ( D ) OTHER INFORMATION: /product="open reading frame"

( i x ) FEATURE:
            ( A ) NAME/KEY: misc_feature
            ( B ) LOCATION: 24..119
            ( D ) OTHER INFORMATION: /product="open reading frame"

( x i ) SEQUENCE DESCRIPTION: SEQ ID NO:1:

| | | | | | | |
|---|---|---|---|---|---|---|
| CCGGGGATCC | GGGTACCATG | GCGGCGCTGG | GCGCCGTGTC | GCACGACTGC | GCCTGCGGCA | 60 |
| CGCTCGACAT | CATCAACAGC | CTCCCCGCCA | AGTGCGGCCT | CCCGCGCGTC | ACCTGCCAGT | 120 |
| GATGGAGATG | GTGTGCCAAG | GTAATTGCGT | TTGCTCGTGC | GAGGATGAGA | AGAGAAGATT | 180 |
| GAATAAGATG | TTTGATGGCA | ACAAGTCATC | AGGCGATCCG | ATCCCTGCAG | CTATGAATGG | 240 |
| GAGTATACGT | AGTAGTGGTC | TCGTTAGCAT | CTGTGTGTCG | CATATGCACG | CCGTGCGTGC | 300 |
| CGTGTCTGTC | CTGCTTGCTC | TGCTGATCGT | TCAATGAACG | ACAAATTAAT | CTAACTCTGG | 360 |
| AGTGACAAGT | CGTTCGAGAT | ATACTAATAC | TACCATGTGC | AGGGTCTTTC | AACCAAAAAA | 420 |
| AAAAAAAAAC | CATGGTACCC | GGATCC | | | | 446 |

( 2 ) INFORMATION FOR SEQ ID NO:2:

( i ) SEQUENCE CHARACTERISTICS:
            ( A ) LENGTH: 347 base pairs
            ( B ) TYPE: nucleic acid
            ( C ) STRANDEDNESS: double
            ( D ) TOPOLOGY: linear ( i i ) MOLECULE TYPE: cDNA to mRNA ( v i ) ORIGINAL SOURCE:
            ( A ) ORGANISM: rice
            ( F ) TISSUE TYPE: anther ( i x ) FEATURE:
            ( A ) NAME/KEY: misc_feature
            ( B ) LOCATION: 1..322
            ( D ) OTHER INFORMATION: /product="cDNA T23"

( i x ) FEATURE:
            ( A ) NAME/KEY: misc_feature
            ( B ) LOCATION: 333..347
            ( D ) OTHER INFORMATION: /product="cloning adaptor
                sequence"

( x i ) SEQUENCE DESCRIPTION: SEQ ID NO:2:

| | | | | | | |
|---|---|---|---|---|---|---|
| AGATGGACAC | CGCCAGATCA | GGGCTCTCGG | CTTCCCGCCA | TTCCTCTCCG | TTCAGCAGAT | 60 |
| GTTCGACGAC | TCGATCAAGA | GCGTCCAGGA | CAAGGGCCTC | CTTCCTCCTC | ATGCTTGATT | 120 |
| CATATGATCC | ACACAATTAA | GCTGCTTGAT | TAATTATAAC | TAATCAAATA | TTGTTAAGGA | 180 |
| TCGGAATCAC | GTAGTACCGA | TCATATATGT | GTTCATCTCG | AAATTAACTG | TAAGTGTGAG | 240 |
| ATCGAGAATA | CACTAATACA | GTGCTAATAT | ATACCGAAAT | GTTTGTAAAA | AAAAAAAAA | 300 |
| AAAAAAAAAA | AAAAAAAAA | AAAAAAAAA | AACCATGGTA | CGGATCC | | 347 |

( 2 ) INFORMATION FOR SEQ ID NO:3:

( i ) SEQUENCE CHARACTERISTICS:

5,639,948

( A ) LENGTH: 294 base pairs
                ( B ) TYPE: nucleic acid
                ( C ) STRANDEDNESS: double
                ( D ) TOPOLOGY: linear ( i i ) MOLECULE TYPE: cDNA to mRNA ( v i ) ORIGINAL SOURCE:
                ( A ) ORGANISM: rice
                ( F ) TISSUE TYPE: anther ( i x ) FEATURE:
                ( A ) NAME/KEY: misc_feature
                ( B ) LOCATION: 1..16
                ( D ) OTHER INFORMATION: /product="cloning adaptor
                        sequence"

( i x ) FEATURE:
                ( A ) NAME/KEY: misc_feature
                ( B ) LOCATION: 17..284
                ( D ) OTHER INFORMATION: /product="cDNA T42"

( i x ) FEATURE:
                ( A ) NAME/KEY: misc_feature
                ( B ) LOCATION: 285..294
                ( D ) OTHER INFORMATION: /product="cloning adaptor
                        sequence"

( x i ) SEQUENCE DESCRIPTION: SEQ ID NO:3:

GAATTCGGTA   CCATGGCGCC   GCCTGCGGCC   TCTCCATCAG   CTTCACCATC   GCCCCCAACA        60

TGGACTGCAA   CCAGGTTACA   GAGGAACTGA   GAATCTGAGA   GCGTGAGGAA   TCGAGTTCAT       120

GTTGCATTTA   TCATCAATCA   TCATCGACTA   GATCAATAAA   TCGAGCAAAG   CTTTGATAAA       180

GAGCGAGCCG   CCTTAATTAA   TTTACAATAA   TCTTGGATGT   CATCCTGCAT   G Y GTGTATGA     240

TCACACGGTT   GTTAATTAG    GCACTTTAAT   TTTGCAAAAA   AAAACCATGG   TACC             294

( 2 ) INFORMATION FOR SEQ ID NO:4:

( i ) SEQUENCE CHARACTERISTICS:
                ( A ) LENGTH: 268 base pairs
                ( B ) TYPE: nucleic acid
                ( C ) STRANDEDNESS: double
                ( D ) TOPOLOGY: linear ( i i ) MOLECULE TYPE: cDNA to mRNA ( v i ) ORIGINAL SOURCE:
                ( A ) ORGANISM: rice
                ( F ) TISSUE TYPE: anther ( i x ) FEATURE:
                ( A ) NAME/KEY: misc_feature
                ( B ) LOCATION: 1..7
                ( D ) OTHER INFORMATION: /product="cloning adaptor
                        sequence"

( i x ) FEATURE:
                ( A ) NAME/KEY: misc_feature
                ( B ) LOCATION: 8..253
                ( D ) OTHER INFORMATION: /product="cDNA T155"

( i x ) FEATURE:
                ( A ) NAME/KEY: misc_feature
                ( B ) LOCATION: 254..268
                ( D ) OTHER INFORMATION: /product="cloning adaptor
                        sequence"

( x i ) SEQUENCE DESCRIPTION: SEQ ID NO:4:

ACCATGGGTT   GTGTTAGCGC   GCGGCAAAAG   TTACCGTCGT   GATCATTTCT   GGGCTACTTC        60

CAGCAGGAGA   TCGGCCTAGC   TGGTGTCTTA   ATTAATTATA   TGTGATGTGC   TGTTCCGTTT       120

TCTGTGATGT   GTGTCATCCG   TTTCATACTC   CGTATCGATC   ATCATTATGT   GTTTCCGGTA       180

| GGAATTTGCG | CTCGATATAT | GGTGATCCAA | AATTTATGAA | TCAATTCTTC | GTGATTCACT | 240 |
| CTGTAAAAAA | AAACCATGGT | ACCCCGGG | | | | 268 |

(2) INFORMATION FOR SEQ ID NO:5:

(i) SEQUENCE CHARACTERISTICS:
        (A) LENGTH: 617 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: rice
        (F) TISSUE TYPE: anther (ix) FEATURE:
        (A) NAME/KEY: misc_feature
        (B) LOCATION: 1..58
        (D) OTHER INFORMATION: /product="cloning adaptor
            sequence"

(ix) FEATURE:
        (A) NAME/KEY: misc_feature
        (B) LOCATION: 59..593
        (D) OTHER INFORMATION: /product="cDNA E1"

(ix) FEATURE:
        (A) NAME/KEY: misc_feature
        (B) LOCATION: 594..617
        (D) OTHER INFORMATION: /product="cloning adaptor
            sequence"

(xi) SEQUENCE DESCRIPTION: SEQ ID NO:5:

| ACAGGTCGAC | TCTAGAGGAT | CCCCGGGCGA | GCTCGAATTC | GAGATCCGGG | TACCATGGGC | 60 |
| AAGAGATCCA | TCAAGCCGTC | GCGATGACGA | CGAGGCCTTC | TGTTTTTCC | ACCGTTGTCG | 120 |
| CGGCGATCGC | CATCGCCGCG | CTGCTGAGCA | GCCTCCTCCT | CCTGCAGGCT | ACCCCGGCCG | 180 |
| CGGCCAGCGC | GAGGGCCTCG | AAGAAGGCTT | CGTGCGACCT | GATGCAGCTG | AGCCCGTGCG | 240 |
| TCAGCGCGTT | CTCCGGTGTG | GGGCAGGGCT | CGCCATCGTC | CGCGTGCTGC | TCCAAGCTCA | 300 |
| AGGCGCAGGG | CTCCAGCTGC | CTGTGCCTCT | ACAAGGACGA | CCCCAAAGTG | AAGCGCATTG | 360 |
| TCAGCTCCAA | TCGCACCAAG | AGGGTCTTCA | CCGCGTGCAA | GGTGCCCGCG | CCGAACTGCT | 420 |
| AAGCCTTTGC | ATTTGACCAT | TGTTCAGTGA | GGCAGAAAAC | CTGTCACCGC | TCGCAGTACT | 480 |
| TCTCTCGAGA | AAATTAGCAG | TAATAAACTC | AGTTGAGTGC | ATAACAATCT | TGGCATGTAC | 540 |
| TGTGCATACA | GTGTACTTCA | AGCTACCCAA | ACTCCGAAGC | AGTTCTGTCT | TCCCCATGGT | 600 |
| ACCCGGATCT | CGAATTC | | | | | 617 |

(2) INFORMATION FOR SEQ ID NO:6:

(i) SEQUENCE CHARACTERISTICS:
        (A) LENGTH: 3627 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Oryza sativa (ix) FEATURE:
        (A) NAME/KEY: promoter
        (B) LOCATION: 1..2845
        (D) OTHER INFORMATION: /function="sequence comprising
            anther- specific PT72 promoter"

( i x ) FEATURE:
    ( A ) NAME/KEY: TATA_signal
    ( B ) LOCATION: 2733..2739

( i x ) FEATURE:
    ( A ) NAME/KEY: misc_feature
    ( B ) LOCATION: 2765
    ( D ) OTHER INFORMATION: /product="transcription
        initiation"

( i x ) FEATURE:
    ( A ) NAME/KEY: misc_feature
    ( B ) LOCATION: 2846
    ( D ) OTHER INFORMATION: /product="ATG start translation of
        T72 gene"

( x i ) SEQUENCE DESCRIPTION: SEQ ID NO:6:

| | | | | | | |
|---|---|---|---|---|---|---|
| GACAATACAT | CAAGTAAATC | AAACATTACA | AATCAGAACC | TGTCTAAGAA | TCCATCTTAA | 60 |
| TTCAGAAAAA | AACTCAGATT | AGATGTTCAT | GCTTCCACCA | GAAGCAGGAA | TGTGCAACCT | 120 |
| ACACTTCCTG | TAATTTCCAT | ACTACAATGT | CCCCACTGAC | CACTGTGCCT | GATGCTCTAT | 180 |
| TAGAATACCA | CATCCTCCAT | GGCTCCATGT | AAATGCATAT | AAATTTGACT | CTTTAAATTA | 240 |
| GTAACTACAA | TTTAAAATTT | ATCGAACATT | GTTCAAATTT | ATAAACAGTT | TCCCCAAATT | 300 |
| TAGATGCTCC | CAAATGTACA | CAGCTACTAG | TAAAGCACCA | TCCAGTTTCA | CCTGAACAGG | 360 |
| ACTGACATAA | ATGTGTGAAA | AGGGGACGTC | ATTCCCCCAA | ATACAACTGA | ACAATCCTCC | 420 |
| ATCAGAACAT | TCATTTGATT | GACATTACTC | GGAGAGATAC | AGCTCGCAGG | CACACGAGAT | 480 |
| TCTTCTGCCT | TTCCAATTGC | CACGAACCCA | CATGTCACAC | GACCAACCAA | AAAGAGAGAA | 540 |
| TTTTTCTTTG | CACAAACAAA | AAGTGAGATT | TTTTTTCGC | CACAAAGGTG | CGAACTTTCT | 600 |
| TCTCTCTCCC | ACTTTCCAAT | CAAGAAACGA | AGCACTCAAA | CCAAGAACAA | ACCAAGGAAG | 660 |
| GAGAGATCGC | TCCCTCTCCC | AGAGCAAACG | AAAGGAGAGA | ACTCAGATGG | ATGCGAACTA | 720 |
| CTACCTTGCC | TCTTTCCCCG | GAGAAGCAGC | GAAGGAGAAG | AGCGCGATGC | CGCCGCCGCC | 780 |
| GCCGCCTCCG | GCAACCTCCG | GCTCCGGCGA | GTCCGCCTCC | TCCTCCTCTC | TCACCTCTCT | 840 |
| CTTCCCAACC | GTGTGGTGTT | CGAGAAGCTT | TTATGCGAGC | GACGTGCAGT | GGAAGCGGTT | 900 |
| GCTCCCAAGT | CAAACTGATG | GAGACCACCT | ACTATCTTCC | TCTTGTTTC | TTCTGCTTTT | 960 |
| CTTTTCTTTA | TCTTTTTTCT | TTCATTTTAT | TTGAGCGAT | GAACTTGAGA | ACAGTTTGGT | 1020 |
| TGTGGGTTAA | ATTAAACGGT | GCAGAATTGC | AAAGCTACGT | CCTTTTCGTC | TGATTAAGGT | 1080 |
| GGTATCAGAA | TCCTAATCTG | TTAGCTCAGC | ATTTGTTTTT | GTGTGTTTAA | TTGGCCATGA | 1140 |
| CATCAGATGG | TTCAGACCGG | TGGCAGGTCT | TCATCGGAGA | GGAGAATGAG | AGCAATGCAA | 1200 |
| GTTGCAAACA | ACAAACAGGT | CCTTCCAAAC | GGGTTGGTTT | CATTCCACAG | AACAGGATAG | 1260 |
| CAACCAGAGC | ACAAACCGTT | CAACAATATA | TATATATA | TATATATA | TATATATA | 1320 |
| TATATATA | TATATATG | ATTTAAAATT | ATATTACTAT | TTTAGGATA | CGGAACTCTT | 1380 |
| AACACATGAA | AATCTAAACA | TTTCAACCA | ATCAGAACTA | CTAGAAAGAT | AATCTAACTA | 1440 |
| CTTCAAAATT | TAAAATTTGA | CAAATAAAT | AACTAGTTTT | TTCTAAAGCT | ATCTTCACTG | 1500 |
| GACAACTTAT | GAATATTTAT | ATTTATGAAG | CGAGTACTCT | CCTAGTACAT | ATTACATATA | 1560 |
| TATTCTTCTT | CTCATGAAAA | ATTAACTTCT | CGCTATAAAT | CCGAACATAT | ATTATGCGTA | 1620 |
| GCAAGTTGTT | TTTTTAACG | GGTGGAGTAA | TATTAGAGTA | TTTAAATTCC | TTCAAATTGC | 1680 |
| CATCCCTCTG | GGACTTTGCT | GCTGTTGTTC | TTCCACGGTT | GCTGTCAGTG | TCACCCAGAT | 1740 |
| TTGCATCCTT | TCCAGCTCGT | AGCTACTGTT | CTGCATGTAT | TGGACTTGGA | TTAAGATCAA | 1800 |
| ATGCAGTTGC | TATTGTAACT | GCACAATAGC | AACTGCACAC | AATCATGTCC | ATTCGTTTTC | 1860 |

-continued

| | | | | | | |
|---|---|---|---|---|---|---|
| AGATCCAACG | GCTCTAGATG | ACTGCTACAG | TACATGCATA | ATAGTACATC | TCTGCTACAG | 1920 |
| TGTTTTTGCT | GCAGTACCAC | TTCATATCCT | GGCCTTCCGT | TCTAGATCAT | GTGATGTACA | 1980 |
| TGTTTTTTTG | AAACAACCCG | CACAAGACAT | TGATAGAGTA | GGAAATGTGA | TGTACATGTT | 2040 |
| AACGGCTTAA | GTTACAGTTA | CAATAACAAC | TGCACAGGAT | CTTGATCCAT | TGGACTTGTA | 2100 |
| TAATATCTCA | TCTCGTCGTT | CCATTATCGT | GGTAACAGTT | GGCAACTTGG | CATCCAGTGC | 2160 |
| TGGAAACTAT | GCCGTGTGTA | CATCAGGATC | GTCCTTTTTG | TTCAGTTCCA | AGATAGAACA | 2220 |
| AGTCCAAAAG | ATGGCCGTAG | TTTTTTTAGT | CACAGTGGAA | GCTGACATAG | CCGTGGAATA | 2280 |
| AGTTCTGCAC | AAAAGTTGCC | ATTCGAGATC | AACTACTGGT | AGTAGTAGTC | ATCTTCTACC | 2340 |
| ACTGCGAATA | TTCGAAGGGA | CACAAAAGA | TCAACGAGTA | AATTAGTTCA | CCGGAAGACG | 2400 |
| ACACATTATC | ACCACAAAAA | GACTAAAAAC | AAAAGAAAT | TGCCAGGCCA | AAAAGGCAA | 2460 |
| AAAAGAAAAA | AAAAGATGGC | ACGAGGCCCA | GGGCTACGGC | CCATCTTGTC | GCCGGCCCAA | 2520 |
| CCGCGCGCGC | GAAACGCTCT | CGTCGGCTCT | CGGCTCGCCG | CGACGCGATG | GAGAGTTCGC | 2580 |
| GCCGCGGCGC | GCGCGCGCGT | TCGGTGGCTC | ACACGCTTGC | GCCCTCGTCC | TCCCGGCCGG | 2640 |
| CGCGGGCGCC | GACCGCGCGT | CCGCCGCATG | CGCGCGGCGT | AGGTGAGCAA | CGCGGGCCTC | 2700 |
| GCCGCGCGCG | CTCCCCTCCT | TCGATCCCCT | CCTATAAATC | GAGCTCGCGT | CGCGTATCGC | 2760 |
| CACCACCACC | ACGACACACA | CGCACGCACC | GTGCAGGCAT | CGACGACGAG | CGAGAGCCCC | 2820 |
| TCGGCGGCAG | AAGACACTCA | CGGCGATGGC | GGTGACGAGG | ACGGCGCTGC | TGGTGGTGTT | 2880 |
| GGTAGCGGGG | GCGATGACGA | TGACGATGCG | CGGGGCGGAG | GCGCAGCAGC | CGAGCTGCGC | 2940 |
| GGCGCAGCTC | ACGCAGCTGG | CGCCGTGCGC | GCGAGTCGGC | GTGGCGCCGG | CGCCGGGGCA | 3000 |
| GCCGCTGCCG | GCGCCCCGG | CGGAGTGCTG | CTCGGCGCTG | GGCGCCGTGT | CGCACGACTG | 3060 |
| CGCCTGCGGC | ACGCTCGACA | TCATCAACAG | CCTCCCCGCC | AAGTGCGGCC | TCCCGCGCGT | 3120 |
| CACCTGCCGT | AAGAAAACGA | ATAAAATCGA | TTTGCTATCT | ATCGATGATT | GTGTTTTTGT | 3180 |
| AGACTAAACT | AAACCCCTAT | TAATAATCAA | CTAACCGATG | AACTGATCGT | TGCAGAGTGA | 3240 |
| TGGAGATGGT | GTGCCAAGGT | AATTGCGTTT | GCTCGTGCGA | GGATGAGAAG | AGAAGATTGA | 3300 |
| ATAAGATGTT | TGATGGCAAC | AAGTCATCAG | GCGATCCGAT | CCCTGCAGCT | ATGAATGGGA | 3360 |
| GTATACGTAG | TAGTGGTCTC | GTTAGCATCT | GTGTGTCGCA | TATGCACGCC | GTGCGTGCCG | 3420 |
| TGTCTGTCCT | GCTTGCTCTG | CTGATCGTTC | AATGAACGAC | AAATTAATCT | AACTCTGGAG | 3480 |
| TGACAAGTCG | TTCGAGATAT | ACTAATACTA | CCATGTGCAG | GGTCTTTCAA | CCAAGGTTCA | 3540 |
| TGTTTTCCAC | GAAAGCCGAT | TGAAACGAAA | CCGCGAAATT | TTGATGCGAG | ATGAAAGCAG | 3600 |
| ATTCCGAGTG | AAATTTTAAA | TGGTTTT | | | | 3627 |

( 2 ) INFORMATION FOR SEQ ID NO:7:

( i ) SEQUENCE CHARACTERISTICS:
        ( A ) LENGTH: 2370 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Oryza sativa ( i x ) FEATURE:
        ( A ) NAME/KEY: promoter
        ( B ) LOCATION: 1..1808
        ( D ) OTHER INFORMATION: /function="anther specific PT42
            promoter"

( i x ) FEATURE:
    ( A ) NAME/KEY: TATA_signal
    ( B ) LOCATION: 1748..1755

( i x ) FEATURE:
    ( A ) NAME/KEY: misc_feature
    ( B ) LOCATION: 1780
    ( D ) OTHER INFORMATION: /product="transcription
        initiation"

( i x ) FEATURE:
    ( A ) NAME/KEY: misc_feature
    ( B ) LOCATION: 1809
    ( D ) OTHER INFORMATION: /product="ATG start translation
        T42"

( x i ) SEQUENCE DESCRIPTION: SEQ ID NO:7:

| | | | | | | |
|---|---|---|---|---|---|---|
| GGCCATCACT | GTCGGGTGCT | GCGCCATGGA | CATCACCGTC | TCCTTCCTGC | GCCGCCGTCG | 60 |
| CCGGTGAGCT | CCAAGGCCGA | AGCCTTCTTC | CCCTCACGCC | ACTACCTCTC | TCTTCCCCAA | 120 |
| TTCCGGCCAA | CGCCGTCCGT | TGCCACAGCG | CCACCTCCAC | GCCATCCCAG | AGCCCCGTGC | 180 |
| CGTGCCACCG | GGTTCGCCTC | CATCTCCTCT | TGCCAACGCC | GACGCTCGTC | GCGGCAGCCA | 240 |
| TGCGCTGTCA | CCGATGAACA | CCGCCGCGCC | ACAGCCATGG | CAGAGCACGG | CCAGGGAGCC | 300 |
| ATGGCTGCTC | TGCCTCCTCC | TCCTTCTCTC | ACATCTGGTT | GCAGCCGGAC | CTAGTCGGCT | 360 |
| TATACAAATG | GCCCATGGGC | AAAATTGTCT | TTATGAAAG | TTTCTCTCAC | CGTTTCAGTC | 420 |
| GGAAATAATA | AATAATGGG | AGGATTGTCC | GCCAGCAAAT | TACCATATTT | TTTCGGTGTC | 480 |
| CAAGAGCAAA | TACACGATCT | TCGGGTGTTT | CACAGCAAAG | ACCACAATTT | CTAAGTGTCC | 540 |
| TGTAACAAAT | TTTGCCAATA | AAAATTTAAA | ACCAAGGAG | AAGACTGTAC | ATGAAGAAAA | 600 |
| ACAAAGAGAA | TGAATTACA | TAAGCTCAGG | GGTTATAAAG | TTGATTTATT | TTAGGATGA | 660 |
| AGGAAGTGTG | TGAAAACAAT | GGCCAATTGG | GTGTCGGAAA | ATATAACGTG | CTTGCTAAAA | 720 |
| TGTCGTCCCC | ATATCCTGTA | GCTGATTATA | GATAGACCCT | GATGGTCAAG | ATGCCCTGTA | 780 |
| CTGGATCGTG | TTTCCATGCT | TCATCTCCGC | TTCTCTCAAG | TACTCCCCGA | ACTCACATAT | 840 |
| CTGGTGGGCT | GGATCCACAG | TAAGAAACAG | TCAAACAACA | CTCACTTCAT | AGATAACCAA | 900 |
| TTGTTTAATT | ATTCTTAGTC | CCTTATCTTA | TACTCCTAGT | AAGTGCTTAA | AAACTTGGTA | 960 |
| TAAATATCAA | ATTTATCGTA | CAATTACAAT | ATAATTATAA | CGTATACCAT | GTAATTTTA | 1020 |
| AAACTATTTT | TAGATAAAAA | AAATATGGTG | ATGAGCAGCC | GCAGCAGCGG | ACGCCGAACC | 1080 |
| ACCTGCCGAA | CATCACCAAG | ATAGCGAGTC | CTAAAAATTT | TTAGTGTTCG | TTTGCTGGGT | 1140 |
| TGGTAACTAA | TTAAAAAAAA | AGAGCGACTC | ATTAGCTCAT | AAATAATTAC | GTATTAGCTA | 1200 |
| ATTTTTTTAA | AAAATAAATT | AATATAACTT | ATAAAGCAGC | TTTTGTATAA | TTTTTTTTT | 1260 |
| AAAAAAGTGT | TGTTTAGCAG | TTTTGGGAAG | TGTGCCGAGG | GAAAACGATG | AGATGGGTTG | 1320 |
| GGGAAGGAGG | GGGAAGAAGT | GAAGAACACA | GCAAATATAG | GCAGCATCGT | CCCGTACAGA | 1380 |
| TCAGGCTGCA | ACCACGCCCC | GCGGAGATAG | TTAACGCGGC | CCACGTTGTG | CTATAGCCCG | 1440 |
| TCACTCTCGC | GGGCCTCTCC | AACCTCCAGT | TTTTTTCTA | GCCCATCAGC | TGATACGGGG | 1500 |
| CCTTCCCCCC | ATGCAGGAGG | ATGGCCCGCC | ACGCGGTGTT | TTGGGCCGTT | CTCGCCGCGC | 1560 |
| GCGCCCGTGC | CGATCCGGGA | CTCATCCCAC | GTGCCGCCTC | GCCACCGCCG | CCGCCGCCGC | 1620 |
| TGCTGCTCCG | GCTGCCGGCT | GGACCTTCAC | GCTCACGCGC | TCTCCCCTGC | CAACCACCA | 1680 |
| CGCAAACAAA | CACGAAGTTC | GCGCCGTCGA | CCGGCTCCCC | TCCTCCCCCG | CGCGCATCGG | 1740 |
| ATCCCCCTAC | ATAAACCCTC | TCGCTCGCCA | TCGCCATGGC | AGCAACTCCC | CTCCTCCACT | 1800 |
| AGACCACCAT | GCACAGATCG | ATGGCCTCTC | AGGCGGTGGC | GCCCCTCCTC | CTCATCCTCA | 1860 |

| | | | | | | |
|---|---|---|---|---|---|---|
| TGCTCGCGGC | GGCGGCGGGG | GGCGCGTCGG | CGGCGGTGCA | GTGCGGGCAG | GTGATGCAGC | 1920 |
| TGATGGCGCC | GTGCATGCCG | TACCTCGCCG | GCGCCCCGG | GATGACGCCC | TACGGCATCT | 1980 |
| GCTGCGACAG | CCTCGGCGTG | CTCAACCGGA | TGGCCCCGGC | CCCCGCCGAC | CGCGTCGCCG | 2040 |
| TCTGCAACTG | CGTCAAGGAC | GCCGCCGCCG | GCTTCCCCGC | CGTCGACTTC | TCCCGCGCCT | 2100 |
| CCGCCCTCCC | CGCCGCCTGC | GGCCTCTCCA | TCAGCTTCAC | CATCGCCCCC | AACATGGACT | 2160 |
| GCAACCAGTA | AGTTCATTCA | TTCTTTCTTA | ACTCCAATTC | AATTTATCCA | TCACCTCGAC | 2220 |
| TTAAGCCTGA | TTAAACTTAA | CTTGTTCTTT | GCATGCTTGC | ACTATTGCAG | GGTTACAGAG | 2280 |
| GAACTGAGAA | TCTGAGAGCG | TGAGGAATCG | AGTTCATGTT | GCATTTATCA | TCAATCATCA | 2340 |
| TCGACTAGAT | CAATAAATCG | AGCAAAGCTT | | | | 2370 |

(2) INFORMATION FOR SEQ ID NO:8:

( i ) SEQUENCE CHARACTERISTICS:
        ( A ) LENGTH: 2407 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Oryza sativa ( i x ) FEATURE:
        ( A ) NAME/KEY: promoter
        ( B ) LOCATION: 1..2263
        ( D ) OTHER INFORMATION: /function="anther-specific
            promoter PE1"

( i x ) FEATURE:
        ( A ) NAME/KEY: TATA_signal
        ( B ) LOCATION: 2181..2187

( i x ) FEATURE:
        ( A ) NAME/KEY: misc_feature
        ( B ) LOCATION: 2111
        ( D ) OTHER INFORMATION: /product="Transcription initiation
            site"

( i x ) FEATURE:
        ( A ) NAME/KEY: misc_feature
        ( B ) LOCATION: 2264
        ( D ) OTHER INFORMATION: /product="ATG start translation of
            E1 gene"

( x i ) SEQUENCE DESCRIPTION: SEQ ID NO:8:

| | | | | | | |
|---|---|---|---|---|---|---|
| TGATAGTGAC | ATACTCACAT | GCTTTGTCAA | TTCAAGTATC | AGTTCTTTTC | ATATTGATTT | 60 |
| CTTAGTTGAT | GAAAGTATAC | ATATTCTTG | CCATCAATTC | TTTTAGTAGG | TACATTTGGA | 120 |
| CACTAGTGGT | CAGGGTTGAA | CTCTTAACTG | GAGTCTCATC | TGATTTGCTT | ATCTGAGACT | 180 |
| GGGTTTGTGC | AAATCCTGTC | ATGAGGCAAG | GTGGACTGTC | AGTCCATGAC | ACTTTGCTAC | 240 |
| TTCTATTAAG | TTCTCGAAAT | CTTTTCCAGT | GTATGTCCGT | TCTCTTTCAA | ATGAATTATT | 300 |
| TATATGTTCT | GACAGCCTCG | CGGTGTACAT | TTCATTTAAC | TTTTGTCTTC | ACAGGGCCTC | 360 |
| TTGGTATTTT | GTTGAGCAGA | TTGGAATCAA | CCTTCTTGTA | GAACTTCTTG | ATGTCGTCGC | 420 |
| TACCCTTTGC | AACTAGATGG | TCAACTTCTG | TCTTATATCT | TTGGTACAAC | ACTGGCAAAG | 480 |
| TGTGCGCGCA | CAAGAATCCT | GTGAAGTAAG | AAATACAAAC | TTGTCATTGT | GAAAGTTTAG | 540 |
| CTTTATATGA | TCTTGACTCT | AAATTGTTTC | TCCTCAGATC | CTTCTGTGTG | ATTGTTTTAT | 600 |
| TAAAATTTAA | TATTTATCTG | GAATACCTAC | CAATATATAG | TAGACTTGTC | AAGCTGCAAG | 660 |
| AACTTCCAAT | CGCCGACAAT | ACCAATAGAG | ATCCAACCAC | CTTAATATCA | TAAACAATCT | 720 |

| | | | | | |
|---|---|---|---|---|---|
| GATTGTTAGT | CCAGAACTAT | ATTGAGTAGT | GAACAACAAT | AGCACATTAA | CATTATGAGG | 780
| ATTATTGGCT | AACTCTGCAA | TTCAATATTC | TGATGCGTCT | AATCTGGTCA | ATTTAGCGC | 840
| TCCAGAAAGA | ATTGCACAAT | CCTTGGACAA | TGTTGGCACT | GGAACTGTTG | CATGTTTTA | 900
| CATCTCTTAT | TAACGTAGCA | AAGGAGTAGA | TTATTATGTA | CCAGGAGAAA | TCTCTTCAGA | 960
| TCCTTTCCAC | ATGCAATGTC | GTAAAGAACA | GATACAGTGT | ACGTTAGTTT | GTAATGGACG | 1020
| GTCAATGCCA | TTTCTCTGAA | GGCATGTTCA | GAGATGATGA | TTTCTGGGAT | CCTTGGAGGG | 1080
| GCCCTGAAAT | TCGGAAACAG | TTAGTTGAGT | TTTAGTACCT | AATGTCTTGC | GTTATACTAC | 1140
| GTGAAATGCC | ATTTCTGTAA | GCTGAGTTTT | CTACCATCTC | CACAGGAAAT | AAAGCTAATA | 1200
| CCTGTCCAAG | AGTGGTGCGG | CATTTGACCA | AATGAAGATC | ACAAGCATGG | CAAGAATGGC | 1260
| AATCTGGCAA | AGGAGCGGAA | TTATATTGTA | TTCTACTACA | TCGAACAGGA | ACCATATCAA | 1320
| TGTTGCCCCA | GCAAGGACCC | CCGCAGATAA | GTTCCTGTTC | TTCCACAGCA | GAATATCCGC | 1380
| AACTGCATAG | CTCCCAACAA | TGAAATCCAA | AACCACATCG | GCTCAGAGAG | AAGTTATGAT | 1440
| AAAAGGCACT | AATTCTGAAT | AATTTCCTAG | AAAGCGAATA | ATAATAGCAC | ACCTTGACCT | 1500
| CCACCAAGAA | GCTTGTGGAT | CGACTTGTGC | CCATGAAATG | GCATTCTGAC | ATTCTGGTCA | 1560
| CTGTCAGAAT | CTCTCGGAAA | ATGAGGAGGC | ATAGCTTCGT | GTGTGTATGT | GTGTGGGATA | 1620
| TTACGCTGCT | AAAACTTTGT | GTTTCTGATC | GATCTGGTTA | GAGAGCATCG | TCTTTATAAG | 1680
| CACTTAAAAA | TGGTAGTATA | ATCTCTCAAG | GAGCCTATAC | TGCCAAGGAA | AGGATAGCTT | 1740
| GGCCTGTGGG | GATTGAGCCG | TTGAAGGGAA | CAAACGAATA | CAGTTACCTT | ACCAGATGTT | 1800
| TGCCACGACA | TGGGCAACGT | CATTGCTAGA | CCAAGAAGGC | AAGAAGCAAA | GTTAGCTGT | 1860
| CAAAAAGAT | ATGCTAGAGG | CTTTCCAGAA | TATGTTCTAT | CTCAGCCAGA | CCAATGGGGG | 1920
| CAAAATTTAC | TACTATTTGC | CATACATTAA | CCACGTAAAA | GTCCTACACT | CAACCTAACT | 1980
| GTTGAACGGT | CCTGTTCTGG | CCAACGGTGA | GAATGCACCT | AATGGACGGG | ACAACACTTC | 2040
| TTTCACCGTG | CTACTGCTAC | ATCCTGTAGA | CGGTGGACGC | GTGAGGTGCT | TTCGCCATGA | 2100
| CCGTCCTTGG | TTGTTGCAGT | CACTTGCGCA | CGCTTGCACC | GTGACTCACC | TGCCACATTG | 2160
| CCCCCGCCGT | CGCCGGCGCC | TACAAAAGCC | ACACACGCAC | GCCGGCCACG | ATAACCCATC | 2220
| CTAGCATCCC | GGTGTCCAGC | AAGAGATCCA | TCAAGCCGTC | GCGATGACGA | CGAGGCCTTC | 2280
| TGTTTTTTCC | ACCGTTGTCG | CGGCGATCGC | CATCGCCGCG | CTGCTGAGCA | GCCTCCTCCT | 2340
| CCTGCAGGCT | ACCCCGGCCG | CGGCCAGCGC | GAGGGCCTCG | AAGAAGGCTT | CGTGCGACCT | 2400
| GATGCAG | | | | | | 2407

( 2 ) INFORMATION FOR SEQ ID NO:9:

( i ) SEQUENCE CHARACTERISTICS:
        ( A ) LENGTH: 5620 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..395
        ( D ) OTHER INFORMATION: /product="pUC18 derived sequence"

( i x ) FEATURE:
        ( A ) NAME/KEY: polyA_site
        ( B ) LOCATION: 396..802
        ( D ) OTHER INFORMATION: /standard_name= "from nopaline
        synthase gene from Agrobacterium T-DNA"

( i x ) FEATURE:
  ( A ) NAME/KEY: promoter
  ( B ) LOCATION: 1139..1683
  ( D ) OTHER INFORMATION: /function=sequence derived from
    " tapetum-specific promoter of Nicotiana tabacum"

( i x ) FEATURE:
  ( A ) NAME/KEY: CDS
  ( B ) LOCATION: 803..1138
  ( D ) OTHER INFORMATION: /product="CDS of barnase gene"

( i x ) FEATURE:
  ( A ) NAME/KEY: promoter
  ( B ) LOCATION: 1684..2515
  ( D ) OTHER INFORMATION: /standard_name= "35S3 promoter
    sequence from Cauliflower mosaic virus CabbB-J"

( i x ) FEATURE:
  ( A ) NAME/KEY: CDS
  ( B ) LOCATION: 2517..3068
  ( D ) OTHER INFORMATION: /product="CDS of phosphinotricin
    acetyltransferase gene"

( i x ) FEATURE:
  ( A ) NAME/KEY: polyA_site
  ( B ) LOCATION: 3069..3356
  ( D ) OTHER INFORMATION: /standard_name= "Agrobacterium
    T-DNA nopaline synthase gene"

( i x ) FEATURE:
  ( A ) NAME/KEY: misc_feature
  ( B ) LOCATION: 3357..5620
  ( D ) OTHER INFORMATION: /product="pUC18-derived sequence"

( x i ) SEQUENCE DESCRIPTION: SEQ ID NO:9:

| | | | | | | |
|---|---|---|---|---|---|---|
| TCGCGCGTTT | CGGTGATGAC | GGTGAAAACC | TCTGACACAT | GCAGCTCCCG | GAGACGGTCA | 60 |
| CAGCTTGTCT | GTAAGCGGAT | GCCGGGAGCA | GACAAGCCCG | TCAGGGCGCG | TCAGCGGGTG | 120 |
| TTGGCGGGTG | TCGGGGCTGG | CTTAACTATG | CGGCATCAGA | GCAGATTGTA | CTGAGAGTGC | 180 |
| ACCATATGCG | GTGTGAAATA | CCGCACAGAT | GCGTAAGGAG | AAAATACCGC | ATCAGGCGCC | 240 |
| ATTCGCCATT | CAGGCTGCGC | AACTGTTGGG | AAGGGCGATC | GGTGCGGGCC | TCTTCGCTAT | 300 |
| TACGCCAGCT | GGCGAAAGGG | GGATGTGCTG | CAAGGCGATT | AAGTTGGGTA | ACGCCAGGGT | 360 |
| TTTCCCAGTC | ACGACGTTGT | AAAACGACGG | CCAGTGAATT | CGAGCTCGGT | ACCCGGGGAT | 420 |
| CTTCCCGATC | TAGTAACATA | GATGACACCG | CGCGCGATAA | TTTATCCTAG | TTTGCGCGCT | 480 |
| ATATTTGTT | TTCTATCGCG | TATTAAATGT | ATAATTGCGG | GACTCTAATC | ATAAAACCC | 540 |
| ATCTCATAAA | TAACGTCATG | CATTACATGT | TAATTATTAC | ATGCTTAACG | TAATTCAACA | 600 |
| GAAATTATAT | GATAATCATC | GCAAGACCGG | CAACAGGATT | CAATCTTAAG | AAACTTTATT | 660 |
| GCCAAATGTT | TGAACGATCT | GCTTCGGATC | CTCTAGAGNN | NNCCGGAAAG | TGAAATTGAC | 720 |
| CGATCAGAGT | TTGAAGAAAA | ATTTATTACA | CACTTTATGT | AAAGCTGAAA | AAAACGGCCT | 780 |
| CCGCAGGAAG | CCGTTTTTTT | CGTTATCTGA | TTTTTGTAAA | GGTCTGATAA | TGGTCCGTTG | 840 |
| TTTTGTAAAT | CAGCCAGTCG | CTTGAGTAAA | GAATCCGGTC | TGAATTTCTG | AAGCCTGATG | 900 |
| TATAGTTAAT | ATCCGCTTCA | CGCCATGTTC | GTCCGCTTTT | GCCCGGGAGT | TTGCCTTCCC | 960 |
| TGTTGAGAA | GATGTCTCCG | CCGATGCTTT | TCCCCGGAGC | GACGTCTGCA | AGGTTCCCTT | 1020 |
| TTGATGCCAC | CCAGCCGAGG | GCTTGTGCTT | CTGATTTTGT | AATGTAATTA | TCAGGTAGCT | 1080 |
| TATGATATGT | CTGAAGATAA | TCCGCAACCC | CGTCAAACGT | GTTGATAACC | GGTACCATGG | 1140 |
| TAGCTAATTT | CTTTAAGTAA | AAACTTTGAT | TTGAGTGATG | ATGTTGTACT | GTTACACTTG | 1200 |
| CACCACAAGG | GCATATATAG | AGCACAAGAC | ATACACAACA | ACTTGCAAAA | CTAACTTTTG | 1260 |
| TTGGAGCATT | TCGAGGAAAA | TGGGGAGTAG | CAGGCTAATC | TGAGGGTAAC | ATTAAGGTTT | 1320 |

| | | | | | |
|---|---|---|---|---|---|
| CATGTATTAA | TTTGTTGCAA | ACATGGACTT | AGTGTGAGGA | AAAAGTACCA | AAATTTTGTC | 1380
| TCACCCTGAT | TTCAGTTATG | GAAATTACAT | TATGAAGCTG | TGCTAGAGAA | GATGTTTATT | 1440
| CTAGTCCAGC | CACCCACCTT | ATGCAAGTCT | GCTTTAGCT | TGATTCAAAA | ACTGATTTAA | 1500
| TTTACATTGC | TAAATGTGCA | TACTTCGAGC | CTATGTCGCT | TTAATTCGAG | TAGGATGTAT | 1560
| ATATTAGTAC | ATAAAAAATC | ATGTTTGAAT | CATCTTTCAT | AAAGTGACAA | GTCAATTGTC | 1620
| CCTTCTTGTT | TGGCACTATA | TTCAATCTGT | TAATGCAAAT | TATCCAGTTA | TACTTAGCTA | 1680
| GATCCTACGC | AGCAGGTCTC | ATCAAGACGA | TCTACCCGAG | TAACAATCTC | CAGGAGATCA | 1740
| AATACCTTCC | CAAGAAGGTT | AAAGATGCAG | TCAAAGATT | CAGGACTAAT | TGCATCAAGA | 1800
| ACACAGAGAA | AGACATATTT | CTCAAGATCA | GAAGTACTAT | TCCAGTATGG | ACGATTCAAG | 1860
| GCTTGCTTCA | TAAACCAAGG | CAAGTAATAG | AGATTGGAGT | CTCTAAAAAG | GTAGTTCCTA | 1920
| CTGAATCTAA | GGCCATGCAT | GGAGTCTAAG | ATTCAAATCG | AGGATCTAAC | AGAACTCGCC | 1980
| GTGAAGACTG | GCGAACAGTT | CATACAGAGT | CTTTTACGAC | TCAATGACAA | GAAGAAAATC | 2040
| TTCGTCAACA | TGGTGGAGCA | CGACACTCTG | GTCTACTCCA | AAAATGTCAA | AGATACAGTC | 2100
| TCAGAAGACC | AAAGGGCTAT | TGAGACTTTT | CAACAAAGGA | TAATTTCGGG | AAACCTCCTC | 2160
| GGATTCCATT | GCCCAGCTAT | CTGTCACTTC | ATCGAAAGGA | CAGTAGAAAA | GGAAGGTGGC | 2220
| TCCTACAAAT | GCCATCATTG | CGATAAAGGA | AAGGCTATCA | TTCAAGATGC | CTCTGCCGAC | 2280
| AGTGGTCCCA | AAGATGGACC | CCCACCCACG | AGGAGCATCG | TGGAAAAAGA | AGACGTTCCA | 2340
| ACCACGTCTT | CAAAGCAAGT | GGATTGATGT | GACATCTCCA | CTGACGTAAG | GGATGACGCA | 2400
| CAATCCCACT | ATCCTTCGCA | AGACCCTTCC | TCTATATAAG | GAAGTTCATT | TCATTTGGAG | 2460
| AGGACACGCT | GAAATCACCA | GTCTCTCTCT | ATAAATCTAT | CTCTCTCTCT | ATAACCATGG | 2520
| ACCCAGAACG | ACGCCCGGCC | GACATCCGCC | GTGCCACCGA | GGCGGACATG | CCGGCGGTCT | 2580
| GCACCATCGT | CAACCACTAC | ATCGAGACAA | GCACGGTCAA | CTTCCGTACC | GAGCCGCAGG | 2640
| AACCGCAGGA | GTGGACGGAC | GACCTCGTCC | GTCTGCGGGA | GCGCTATCCC | TGGCTCGTCG | 2700
| CCGAGGTGGA | CGGCGAGGTC | GCCGGCATCG | CCTACGCGGG | CCCCTGGAAG | GCACGCAACG | 2760
| CCTACGACTG | GACGGCCGAG | TCGACCGTGT | ACGTCTCCCC | CCGCCACCAG | CGGACGGGAC | 2820
| TGGGCTCCAC | GCTCTACACC | CACCTGCTGA | AGTCCCTGGA | GGCACAGGGC | TTCAAGAGCG | 2880
| TGGTCGCTGT | CATCGGGCTG | CCCAACGACC | CGAGCGTGCG | CATGCACGAG | GCGCTCGGAT | 2940
| ATGCCCCCCG | CGGCATGCTG | CGGGCGGCCG | GCTTCAAGCA | CGGGAACTGG | CATGACGTGG | 3000
| GTTTCTGGCA | GCTGGACTTC | AGCCTGCCGG | TACCGCCCCG | TCCGGTCCTG | CCCGTCACCG | 3060
| AGATCTGATC | TCACGCGTCT | AGGATCCGAA | GCAGATCGTT | CAAACATTTG | GCAATAAAGT | 3120
| TTCTTAAGAT | TGAATCCTGT | TGCCGGTCTT | GCGATGATTA | TCATATAATT | TCTGTTGAAT | 3180
| TACGTTAAGC | ATGTAATAAT | TAACATGTAA | TGCATGACGT | TATTTATGAG | ATGGGTTTTT | 3240
| ATGATTAGAG | TCCCGCAATT | ATACATTTAA | TACGCGATAG | AAAACAAAAT | ATAGCGCGCA | 3300
| AACTAGGATA | AATTATCGCG | CGCGGTGTCA | TCTATGTTAC | TAGATCGGGA | AGATCCTCTA | 3360
| GAGTCGACCT | GCAGGCATGC | AAGCTTGGCG | TAATCATGGT | CATAGCTGTT | TCCTGTGTGA | 3420
| AATTGTTATC | CGCTCACAAT | TCCACACAAC | ATACGAGCCG | GAAGCATAAA | GTGTAAAGCC | 3480
| TGGGGTGCCT | AATGAGTGAG | CTAACTCACA | TTAATTGCGT | TGCGCTCACT | GCCCGCTTTC | 3540
| CAGTCGGGAA | ACCTGTCGTG | CCAGCTGCAT | TAATGAATCG | GCCAACGCGC | GGGGAGAGGC | 3600
| GGTTTGCGTA | TTGGGCGCTC | TTCCGCTTCC | TCGCTCACTG | ACTCGCTGCG | CTCGGTCGTT | 3660
| CGGCTGCGGC | GAGCGGTATC | AGCTCACTCA | AAGGCGGTAA | TACGGTTATC | CACAGAATCA | 3720

-continued

| | | | | | |
|---|---|---|---|---|---|
| GGGGATAACG | CAGGAAAGAA | CATGTGAGCA | AAAGGCCAGC | AAAAGGCCAG | GAACCGTAAA | 3780
| AAGGCCGCGT | TGCTGGCGTT | TTTCCATAGG | CTCCGCCCCC | CTGACGAGCA | TCACAAAAAT | 3840
| CGACGCTCAA | GTCAGAGGTG | GCGAAACCCG | ACAGGACTAT | AAAGATACCA | GGCGTTTCCC | 3900
| CCTGGAAGCT | CCCTCGTGCG | CTCTCCTGTT | CCGACCCTGC | CGCTTACCGG | ATACCTGTCC | 3960
| GCCTTTCTCC | CTTCGGGAAG | CGTGGCGCTT | TCTCAATGCT | CACGCTGTAG | GTATCTCAGT | 4020
| TCGGTGTAGG | TCGTTCGCTC | CAAGCTGGGC | TGTGTGCACG | AACCCCCCGT | TCAGCCCGAC | 4080
| CGCTGCGCCT | TATCCGGTAA | CTATCGTCTT | GAGTCCAACC | CGGTAAGACA | CGACTTATCG | 4140
| CCACTGGCAG | CAGCCACTGG | TAACAGGATT | AGCAGAGCGA | GGTATGTAGG | CGGTGCTACA | 4200
| GAGTTCTTGA | AGTGGTGGCC | TAACTACGGC | TACACTAGAA | GGACAGTATT | TGGTATCTGC | 4260
| GCTCTGCTGA | AGCCAGTTAC | CTTCGGAAAA | AGAGTTGGTA | GCTCTTGATC | CGGCAAACAA | 4320
| ACCACCGCTG | GTAGCGGTGG | TTTTTTTGTT | TGCAAGCAGC | AGATTACGCG | CAGAAAAAAA | 4380
| GGATCTCAAG | AAGATCCTTT | GATCTTTTCT | ACGGGGTCTG | ACGCTCAGTG | GAACGAAAAC | 4440
| TCACGTTAAG | GGATTTTGGT | CATGAGATTA | TCAAAAGGA | TCTTCACCTA | GATCCTTTTA | 4500
| AATTAAAAAT | GAAGTTTTAA | ATCAATCTAA | AGTATATATG | AGTAAACTTG | GTCTGACAGT | 4560
| TACCAATGCT | TAATCAGTGA | GGCACCTATC | TCAGCGATCT | GTCTATTTCG | TTCATCCATA | 4620
| GTTGCCTGAC | TCCCCGTCGT | GTAGATAACT | ACGATACGGG | AGGGCTTACC | ATCTGGCCCC | 4680
| AGTGCTGCAA | TGATACCGCG | AGACCACGC | TCACCGGCTC | CAGATTATC | AGCAATAAAC | 4740
| CAGCCAGCCG | GAAGGGCCGA | GCGCAGAAGT | GGTCCTGCAA | CTTTATCCGC | CTCCATCCAG | 4800
| TCTATTAATT | GTTGCCGGGA | AGCTAGAGTA | AGTAGTTCGC | CAGTTAATAG | TTTGCGCAAC | 4860
| GTTGTTGCCA | TTGCTACAGG | CATCGTGGTG | TCACGCTCGT | CGTTGGTAT | GGCTTCATTC | 4920
| AGCTCCGGTT | CCCAACGATC | AAGGCGAGTT | ACATGATCCC | CCATGTTGTG | CAAAAAAGCG | 4980
| GTTAGCTCCT | TCGGTCCTCC | GATCGTTGTC | AGAAGTAAGT | TGGCCGCAGT | GTTATCACTC | 5040
| ATGGTTATGG | CAGCACTGCA | TAATTCTCTT | ACTGTCATGC | CATCCGTAAG | ATGCTTTTCT | 5100
| GTGACTGGTG | AGTACTCAAC | CAAGTCATTC | TGAGAATAGT | GTATGCGGCG | ACCGAGTTGC | 5160
| TCTTGCCCGG | CGTCAATACG | GGATAATACC | GCGCCACATA | GCAGAACTTT | AAAAGTGCTC | 5220
| ATCATTGGAA | AACGTTCTTC | GGGGCGAAAA | CTCTCAAGGA | TCTTACCGCT | GTTGAGATCC | 5280
| AGTTCGATGT | AACCCACTCG | TGCACCCAAC | TGATCTTCAG | CATCTTTTAC | TTTCACCAGC | 5340
| GTTTCTGGGT | GAGCAAAAAC | AGGAAGGCAA | AATGCCGCAA | AAAAGGGAAT | AAGGGCGACA | 5400
| CGGAAATGTT | GAATACTCAT | ACTCTTCCTT | TTTCAATATT | ATTGAAGCAT | TTATCAGGGT | 5460
| TATTGTCTCA | TGAGCGGATA | CATATTTGAA | TGTATTTAGA | AAAATAAACA | AATAGGGGTT | 5520
| CCGCGCACAT | TTCCCCGAAA | AGTGCCACCT | GACGTCTAAG | AAACCATTAT | TATCATGACA | 5580
| TTAACCTATA | AAAATAGGCG | TATCACGAGG | CCCTTTCGTC | | | 5620

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TGGCCATGGA GGGTAACCTC CGAAGCAGAT CGTTCA        36

( 2 ) INFORMATION FOR SEQ ID NO:11:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

| | |
|---|---:|
| CGAATTCATA TGCACGTGTT CCCGATCTAG TAACAT | 3 6 |

( 2 ) INFORMATION FOR SEQ ID NO:12:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

| | |
|---|---:|
| CGGCAGAAGA CACTCACGGC GATGAAAAAA GCAGTCATTA AC | 4 2 |

( 2 ) INFORMATION FOR SEQ ID NO:13:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

| | |
|---|---:|
| GGGGGTTACC TTAAGAAAGT ATGATGGTGA | 3 0 |

( 2 ) INFORMATION FOR SEQ ID NO:14:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

| | |
|---|---:|
| TGGCCATGGA GCTAGCGGCC GCCACAGAAC AGGATAGCAA | 4 0 |

( 2 ) INFORMATION FOR SEQ ID NO:15:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

| | |
|---|---:|
| TGGCCATGGT TATAGAGAGA GAGATAGATT T | 3 1 |

( 2 ) INFORMATION FOR SEQ ID NO:16:

( i ) SEQUENCE CHARACTERISTICS:
    ( A ) LENGTH: 31 base pairs
    ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:16:

GAAGCTAGCA ATCCCACCAA AACCTGAACC T 31

(2) INFORMATION FOR SEQ ID NO:17:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:17:

GAGATCCATC AAGCCGTCGC GATGAAAAAA GCAGTCATTA AC 42

(2) INFORMATION FOR SEQ ID NO:18:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

TGGCCATGGA GCTAGCGGCC GCAGATCCTT CTGTGTGATT G 41

(2) INFORMATION FOR SEQ ID NO:19:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

CAACTCCCCT CCTCCACTAG ACCACCATGA AAAAGCAGT CATTAAC 47

(2) INFORMATION FOR SEQ ID NO:20:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

GCTAGCGGCC GCATGGCAGA GCACGGCCAG 30

(2) INFORMATION FOR SEQ ID NO:21:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:21:

ATTATAGAGA GAGAGATAGA TTT 23

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GCAATCCCAC CAAAACCTGA ACCT 24

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

ATTCCACAGA ACAGGATAGC 20

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GCCGTGAGTG TCTTCTGCCG 20

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CCATGGCAGA GCACGGCCAG 20

( 2 ) INFORMATION FOR SEQ ID NO:26:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GTGGTCTAGT GGAGGAGGGG AGTTG 25

( 2 ) INFORMATION FOR SEQ ID NO:27:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:27:

```
CCTCAGATCC TTCTGTGTGA                                                     20
```

( 2 ) INFORMATION FOR SEQ ID NO:28:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:28:

```
GCGACGGCTT GATGGATCTC TTGC                                                24
```

( 2 ) INFORMATION FOR SEQ ID NO:29:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:29:

```
CGGCAGAAGA CACTCACGGC GATGGTACCG GTTATCAACA CG                            42
```

( 2 ) INFORMATION FOR SEQ ID NO:30:

( i ) SEQUENCE CHARACTERISTICS:
  ( A ) LENGTH: 47 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:30:

```
CAACTCCCCT CCTCCACTAG ACCACCATGG TACCGGTTAT CAACACG                       47
```

( 2 ) INFORMATION FOR SEQ ID NO:31:

( i ) SEQUENCE CHARACTERISTICS:
  ( A ) LENGTH: 42 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:31:

```
GAGATCCATC AAGCCGTCGC GATGGTACCG GTTATCAACA CG                            42
```

( 2 ) INFORMATION FOR SEQ ID NO:32:

( i ) SEQUENCE CHARACTERISTICS:
  ( A ) LENGTH: 34 base pairs
  ( B ) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:32:

GGGGGTTACC TTATCTGATT TTTGTAAAGG TCTG 34

(2) INFORMATION FOR SEQ ID NO:33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGAATTCAAG CTTGACGTCA GGTGGCACTT 30

(2) INFORMATION FOR SEQ ID NO:34:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

TGGGGAGTAA GCTCGAGCCA AAAAGGATCT TCACCTAG 38

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GGAATTCTGA TCAGGCCAAC GCGCGGGGAG A 31

(2) INFORMATION FOR SEQ ID NO:36:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

TCTTAATACG ATCAATGGCT CGAGTCTCAT GACCAAAATC CCTTA 45

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CGGCTCGAGC TTACTCCCCA T        21

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CCGCTCGAGC CATTGATCGT ATTAAGA        27